(12) United States Patent
Rueckle et al.

(10) Patent No.: US 7,683,078 B2
(45) Date of Patent: Mar. 23, 2010

(54) ARYLSULFONAMIDE DERIVATIVES AS C-JUN-N-TERMINAL KINASES (JNK'S) INHIBITORS

(75) Inventors: Thomas Rueckle, Plan-les-Ouates (CH); Jean-Pierre Gotteland, Beaumont (FR); Russel J. Thomas, Boars Hill Oxford (GB); Marco Biamonte, San Diego, CA (US)

(73) Assignee: Laboratoires Serono S.A., Coinsins (CH)

( * ) Notice: Subject to any disclaimer, the term of this patent is extended or adjusted under 35 U.S.C. 154(b) by 743 days.

(21) Appl. No.: 10/484,744

(22) PCT Filed: Jul. 15, 2002

(86) PCT No.: PCT/EP02/07832

§ 371 (c)(1),
(2), (4) Date: Jun. 30, 2004

(87) PCT Pub. No.: WO03/010164

PCT Pub. Date: Feb. 6, 2003

(65) Prior Publication Data

US 2004/0248886 A1 Dec. 9, 2004

(30) Foreign Application Priority Data

Jul. 23, 2001 (EP) .................... 01116798.8

(51) Int. Cl.
  *C07D 411/12* (2006.01)
  *C07D 409/12* (2006.01)
  *C07D 333/32* (2006.01)
  *A61K 31/445* (2006.01)
  *A61K 31/44* (2006.01)
  *A61K 31/40* (2006.01)
  *A61K 31/38* (2006.01)

(52) U.S. Cl. ............... 514/326; 514/342; 514/422; 514/446; 546/213; 546/281.4; 548/527; 549/65

(58) Field of Classification Search ............ 514/342, 514/326, 422, 426; 546/281.4, 213; 548/527; 549/65

See application file for complete search history.

(56) References Cited

U.S. PATENT DOCUMENTS

| 3,812,144 A | 5/1974 | Dietrich et al. |
| 5,744,320 A | 4/1998 | Sherf et al. |

FOREIGN PATENT DOCUMENTS

| EP | 1 085 011 | 3/2001 |
| EP | 1 088 815 | 4/2001 |
| WO | 00/35906 | 6/2000 |
| WO | 00/35909 | 6/2000 |
| WO | 00/35921 | 6/2000 |
| WO | 00/64872 | 11/2000 |
| WO | 00/75118 | 12/2000 |
| WO | 01/12609 | 2/2001 |
| WO | 01/12621 | 2/2001 |
| WO | 01 23378 | 4/2001 |
| WO | 01 23379 | 4/2001 |
| WO | 01 23382 | 4/2001 |
| WO | 01/47920 | 7/2001 |
| WO | WO 01/72685 A2 | 10/2001 |

OTHER PUBLICATIONS

Roger J. Davis. Cell , vol. 103, pp. 239-252, Oct. 13, 2000.
Yi-Rong Chen, et al., International Journal of Oncology,16:651-662 2000.
Y Tony Lp, et al., Current Opinion in Cell Biology, 10:205-219 1998.
Sirpa Leppä, et al., Oncogene, vol. 18, No. 45, pp. 6158-6162 Nov. 1, 1999.
Audrey Minden, et al., Biochimica et Biophysica Acta, 1333:F85-F104 1997.
A.J. Whitmarsh, et al., J. Mol. Med. 74:589-607 1996.
Shashi Gupta, et al., The EMBO Journal, vol. 15, No. 11, pp. 2760-2770 1996.
Derek D. Yang, et al., Nature, vol. 389, pp. 865-876 Oct. 23, 1997.
Joel H. Martin, et al., Molecular Brain Research, 35:47-57 1996.
Yoshihiro Kumagae, et al., Molecular Brain Research, 67:10-17 1999.
Calin D. Dumitru, et al., Cell, vol. 103, pp. 1071-1083 Dec. 22, 2000.
Zuoning Han, et al., The Journal of Clinical Investigation, vol. 108, No. 1, pp. 73-81 2001.
Hiroshi Nishina, et al., J. Exp. Med. vol. 186, No. 6, pp. 941-953 Sep. 15, 1997.
Stephan J. Kemplak, et al., The Journal of Immunology,162:3176-3187 1999.

(Continued)

*Primary Examiner*—Peter G O'Sullivan
(74) *Attorney, Agent, or Firm*—Oblon, Spivak, McClelland, Maier & Neustadt, L.L.P.

(57) ABSTRACT

The present invention relates to sulfonamide derivatives of formula (I) notably for use as pharmaceutically active compounds, as well as to pharmaceutical formulations containing such sulfonamide derivatives. Said sulfonamide derivatives are useful in the treatment of neuronal disorders, autoimmune diseases, cancer and cardiovascular diseases. Furthermore, said sulfonamide derivatives are efficient modulators of the JNK pathway, they are in particular efficient and selective inhibitors of JNK2 and -3. The present invention is furthermore related to novel sulfonamide derivatives as well as to methods of their preparation. Formula (I) IAr$^1$ is a substituted or unsubstituted aryl or heteroaryl group; X is O or S, preferably O; Ar$^2$ a substituted or unsubstituted arylene or heteroarylene group; R$^1$ and R$^2$ are independently selected from the group consisting of hydrogen and a $C_1$-$C_6$-alkyl group.

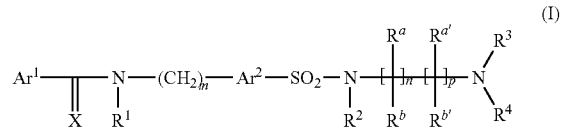

13 Claims, No Drawings

OTHER PUBLICATIONS

S. M. de la Monte, et al., Journal of Alzheimer's Disease, 2:261-281 2000.
Xiongwei Zhu, et al., Journal of Neurochemistry, 76:435-441 2001.
Thomas Force, et al., Circulation Research, 78:947-953 1996.
Shokei Kim, et al., Circulation 97:1731-1737 1998.
Qingbo Xu, et al., The Journal of Clinical Investigation, vol. 97, No. 2, pp. 508-514 1996.
Marie A. Bogoyevitch, et al., Circulation Research, 79:162-173 1996.
Celia M. Pombo, et al., The Journal of Biological Chemistry, vol. 269, No. 42, pp. 26546-26551 Oct. 21, 1994.
Ichiro Onishi, et al., Febs Letters, 420:201-204 1997.
Robert Safirstein, Advances in Renal Replacement Therapy, vol. 4, No. 2, Suppl. 1,pp. 38-42 1997.
Laura Butterfield, et al., The Journal of Biological Chemistry, vol. 272, No. 15, pp. 10110-10116 Apr. 11, 1997.
Mickey C-T Hu, et al., Oncogene, 15:2277-2287 1997.
Xiao Xu, et al., Oncogene 13:135-142 1996.
Yi-Rong Chen, et al., International Journal of Oncology, 16:651-662 2000.
Thomas C. Harding, et al., The Journal of Biological Chemistry, vol. 276, No. 7, pp. 4531-4534 Feb. 16, 2001.
Ahmed F. Abdel-Magid, et al., J.Org. Chem., 61:3849-3862 1996.
Li Xu, et al., Strategies, vol. 10, pp. 1-3 2001.
Shuichan Xu, et al., Proc. Natl. Acad.Sci. USA vol. 93, pp. 5291-5295 1996.
Mausumee Guha & Nigel Mackman, Cellular Signalling, 13:85-94 2001.
A. Fomsgaard, et al., APMIS 98:529-534 1990.
A. Jackie Hunter, et al., TiPS, vol. 16, pp. 123-128 1995.
F. Block, Progress in Neurobiology, vol. 58, pp. 279-295, 1999.
Susan C. Gerhardt & Carl A. Boast, Behavioral Neuroscience, vol. 102, No. 2, pp. 301-303 1988.
S. Scheibye, et al., Bull. Soc. Chim. Belg. vol. 87, pp. 229-238 1978.

ARYLSULFONAMIDE DERIVATIVES AS C-JUN-N-TERMINAL KINASES (JNK'S) INHIBITORS

FIELD OF THE INVENTION

The present invention is related to novel sulfonamide derivatives as well as to methods of their preparation. The present invention is further related to sulfonamide derivatives for use as pharmaceutically active compounds, as well as pharmaceutical formulations containing such sulfonamide derivatives. In particular, the present invention is related to sulfonamide derivatives useful in the treatment and/or prevention of apoptosis related disorders and inflammatory diseases. Furthermore, the present invention is related to sulfonamide derivatives displaying a substantial modulatory, notably an inhibitory, activity of the c-Jun-N-Terminal Kinases (JNKs) function or pathways respectively.

BACKGROUND OF THE INVENTION

Mammalian cells respond to some extracellular stimuli by activating signaling cascades which are mediated by various mitogen-activated protein kinases (MAPKs). Despite the differences in their response to upstream stimuli, the MAP kinase cascades are organized in a similar fashion, consisting of MAP kinase kinase kinases (MAPKKK or MEKK), MAP kinase kinases (MAPKK or MKK) and MAP kinases (MAPK). MAP kinases are a broad family of kinases which includes c-Jun N-Terminal kinases (JNKs), also known as "stress-activated protein kinases" (SAPKs), as well as extracellular signal regulated kinases (ERKs) and p38 MAP kinases. Each of these three MAP kinases sub-families is involved in at least three different but parallel pathways conveying the information triggered by external stimuli. The JNK signaling pathway is activated by exposure of cells to environmental stress—such as chemical toxins, radiation, hypoxia and osmotic shock—as well as by treatment of cells with growth factors or pro-inflammatory cytokines—such as tumour necrosis factor alpha (TNF-α) or interleukin-1 beta (IL-1β).

Two MAP kinase kinases (known as MKKs or MAPKKs), i.e. MKK4 (known also as JNKK1) and MKK7, activate JNK by a dual phosphorylation of specific threonine and tyrosine residues located within a Thr-Pro-Tyr motif on the activation loop on the enzyme, in response to cytokines and stress signals. Even further upstream in the signaling cascade, MKK4 is known to be activated itself also by a MAP kinase kinase kinase, MEKK1 through phosphorylation at serine and threonine residues.

Once activated, JNK binds to the N-terminal region of transcription factor targets and phosphorylates the transcriptional activation domains resulting in the up-regulation of expression of various gene products, which can lead to apoptosis, inflammatory responses or oncogenic processes (1-5).

Some transcription factors known to be JNK substrates are the Jun proteins (c-jun, JunB and JunD), the related transcription factors ATF2 and ATFa, Ets transcription factors such as Elk-1 and Sap-1, the tumor suppressor p53 and a cell death domain protein (DENN).

Three distinct JNK enzymes have been identified as products of the genes JNK1, JNK2 and JNK3 and ten different isoforms of JNK have been identified (3, 6, 7). JNK1 and -2 are ubiquitously expressed in human tissues, whereas JNK3 is selectively expressed in the brain, heart and testes (7, 8, 9, 10). Each isoform binds to the substrates with different affinities, suggesting, in vivo, a substrate specific regulation of the signaling pathways by the different JNK isoforms.

Activation of the JNK pathway has been documented in a number of disease processes, thus providing a rationale for targeting this pathway for drug discovery. In addition, molecular genetic approaches have validated the pathogenic role of this pathway in several diseases.

For example, auto-immune and inflammatory diseases derive from the inappropriate activation of the immune system. Activated immune cells express many genes encoding inflammatory molecules, including cytokines, growth factors, cell surface receptors, cell adhesion molecules and degradative enzymes. Many of these genes are known to be regulated by the JNK pathway, through the activation of the transcription factors c-Jun and ATF-2.

The inhibition of JNK activation in bacterial lipopolysaccharide-stimulated macrophages, effectively modulates the production of the key pro-inflammatory cytokine, TNF-α (11).

The inhibition of JNK activation decreases the transcription factor activation responsible of the inducible expression of matrix metalloproteinases (MMPs) (12), which are known to be responsible of the promotion of cartilage and bone erosion in rheumatoid arthritis and of generalized tissue destruction in other auto-immune diseases.

The JNK cascade is also activated in T cells by antigen stimulation and CD28 receptor co-stimulation (13) and regulates the production of the IL-2 promoter (14). Inappropriate activation of T lymphocytes initiates and perpetuates many auto-immune diseases, including asthma, inflammatory bowel syndrome and multiple sclerosis.

In neurons vulnerable to damage from Alzheimer's disease and in CA1 neurons of patients with acute hypoxia (15), JNK3 protein is highly expressed. The JNK3 gene was also found to be expressed in the damaged regions of the brains of Alzheimer's patients (16). In addition, neurons from JNK3 KO mice were found to become resistant to kainic acid induced neuronal apoptosis compared to neurons from wild-type mice (8).

Based on these findings, the JNK signaling pathway and especially that of JNK2 and JNK3, is thought to be implicated in apoptosis-driven neurodegenerative diseases such as Alzheimer's disease, Parkinson's disease, epilepsy and seizures, Huntington's disease, traumatic brain injuries as well as ischemic and hemorrhaging strokes.

Cardiovascular diseases, such as atherosclerosis and restenosis result from defective regulation of growth of the blood vessel wall. The JNK pathway is activated by atherogenic stimuli and regulates local cytokine and growth factor production in vascular cells (17, 18) inducing pro-atherosclerotic gene (19).

Ischemia alone or coupled with reperfusion in the heart, liver, kidney or brain results in cell death and scar formation, which can ultimately lead to congestive heart failure, hepatic disorders, renal failure or cerebral dysfunction. The JNK pathway is activated by ischemia and reperfusion in the heart (20), leading to the activation of JNK-responsive genes and leukocyte-mediated tissue damage. JNK activation is also observed in kidney (21) or liver (22) following ischemia and reperfusion. The down-regulation of JNKs has been proven to improve renal function and longterm outcome during nephritic and ischemic renal failure (23).

Cancer is characterized by uncontrolled growth, proliferation and migration of cells. In early lung cancer, expression of c-jun is altered and may mediate growth factor signaling in non-small cell lung cancer (24). In addition to regulating c-jun production and activity, JNK activation can regulate phosphorylation of p53, and thus can modulate cell cycle progression (25). Moreover, the role of JNK activation in HTLV-1 (human T cell leukemia virus type 1) mediated tumorgenesis (26) suggests the potential use of JNK inhibitors in cancer treatment (27). Selective inhibition of JNK activation by a naturally occurring JNK inhibitory protein, called JNK-interacting-protein-1 (JIP1), blocks cellular transformation (28). Thus, JNK inhibitors may block transformation and tumor cell growth.

Several small molecules have been proposed as modulators of JNK pathway.

Aryl-oxindole derivatives of respectively the generic formula (A) (WO 00/35909; WO 00/35906; WO 00/35921) and formula (13) (WO 00/64872) have been developed for the treatment of neurodegenerative diseases, inflammation and solid tumors for formula (A) and for the treatment of a broad range of disorders including, neurodegenerative diseases, inflammatory and autoimmune diseases, cardiovascular and bone disorders for formula (B).

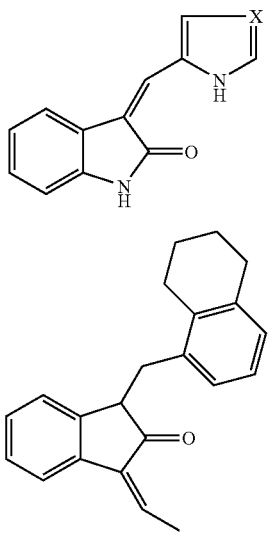

(A)

(B)

Pyrazoloanthrones derivatives of formula (C) have been reported to inhibit JNK for the treatment of neurological degenerative diseases, inflammatory and auto-immune disorders as well as cardiovascular pathologies (WO 01/12609).

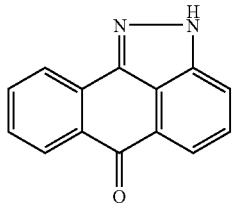

(C)

Tetrahydro-pyrimidine derivatives of formula (D) were reported to be JNK inhibitors useful in the treatment of a wide range of diseases including neurodegenerative diseases, inflammatory and auto-immune disorders, cardiac and destructive bone pathologies (WO 00/75118).

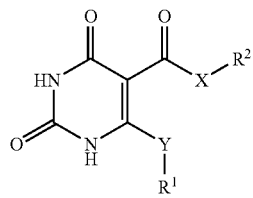

(D)

Other heterocyclic compounds of formula (E) have been proposed to inhibit protein kinases and especially c-Jun-N-Terminal kinases (WO 01/12621) for treating "JNK-mediated conditions" including neurodegenerative diseases, inflammatory and auto-immune disorders, destructive bone disorders, cardiovascular and infectious diseases.

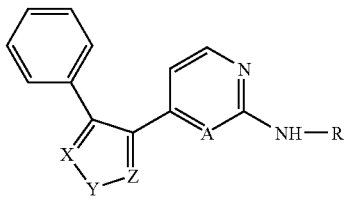

(E)

Benzazoles derivatives such as represented by formula (F) (WO 01/47920) have been described as modulators of the JNK pathway and especially as selective inhibitors of JNK2 and/or JNK3 for the treatment of neuronal disorders, auto-immune diseases, cancers and cardiovascular diseases.

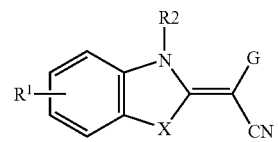

(F)

Several sulphonamide derivatives of formula (G) (WO 01/23378), sulfonyl amino acid derivatives of formula (H) (WO 01/23379) and sulfonyl hydrazide derivatives of formula (J) (WO 01/23382), were also developed to inhibit JNKs especially JNK2 and JNK3 for treating neurodegenerative diseases, auto-immune disorders, cancers and cardiovascular diseases.

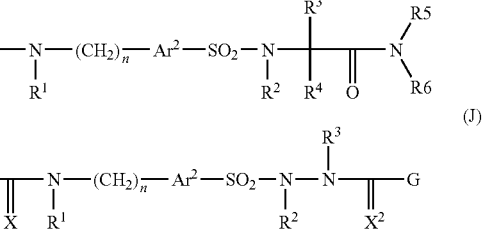

(G)

(H)

(J)

The high relevance of the JNK pathway in some widely spread diseases stresses the need to develop inhibitors, preferentially selective, of JNKs, including JNK3 inhibitors.

SUMMARY OF THE INVENTION

It is an objective of the present invention to provide molecules which are suitable for the treatment of a variety of diseases, in particular of neuronal or the autoimmune system related disorders, cancer, ischemic conditions and cardiovascular diseases.

It is notably an objective of the present invention to provide chemical compounds which are able to modulate, preferably to down-regulate or to inhibit the JNK (Jun kinase) pathway so to be useful in method of treating diseases which involve the JNK pathway.

Moreover, it is an objective of the present invention to provide methods for preparing said chemical compounds. It is furthermore an objective of the present invention to provide a new category of pharmaceutical formulations for the treatment of diseases, in particular those mediated by the JNK function.

It is finally an objective of the present invention to provide a method for the treatment and/or prevention of diseases that are caused by disorders of the autoimmune and/or the neuronal system.

In a first aspect, the invention provides compounds of formula I:

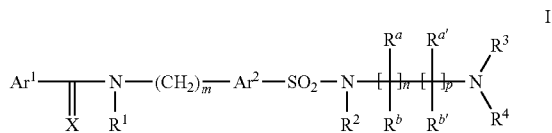

Wherein:
Ar$^1$ is selected from substituted or unsubstituted aryl or heteroaryl groups;
Ar$^2$ is selected from substituted or unsubstituted arylene or heteroarylene groups;
X is O or S, preferably O;
R$^1$ and R$^2$ are independently selected from the group consisting of hydrogen and C$_1$-C$_6$-alkyl group;
R$^a$, R$^{a'}$, R$^b$, R$^{b'}$ are independently selected from the group consisting of hydrogen and C$_1$-C$_6$-alkyl; or alternatively R$^1$ and R$^a$ or R$^b$ form, together with the carbon atoms to which they are linked, a substituted or unsubstituted 5-8-membered saturated, partially unsaturated or aromatic ring containing optionally one or more heteroatoms selected from O, N, S;
R$^3$ is selected from the group consisting of H, C$_1$-C$_{10}$-alkyl, C$_2$-C$_{10}$-alkenyl, C$_2$-C$_{10}$-alkynyl, aryl or heteroaryl, 3-8 membered cycloalkyl optionally containing 1-3 heteroatoms selected from N, O, S, aryl C$_1$-C$_{10}$-alkyl and heteroaryl C$_1$-C$_{10}$-alkyl;
or R$^3$ and R$^a$ or R$^a$ form, together with the N atom linked to R$^3$ a 5-8-membered saturated ring containing optionally at least one further heteroatom selected from O, N, S;
R$^4$ is selected from the group consisting of H and —C(H) R$^5$R$^6$;
R$^5$ and R$^6$ are independently selected from the group consisting of H, C$_1$-C$_{10}$-alkyl, C$_2$-C$_{10}$-alkenyl, C$_2$-C$_{10}$-alkynyl, aryl or heteroaryl, 3-8 membered cycloalkyl optionally containing 1-3 heteroatoms selected from N, O, S, aryl C$_1$-C$_{10}$-alkyl and heteroaryl C$_1$-C$_{10}$-alkyl;
m is an integer from 1 to 5, preferably between 1-3 and most preferably 1;
n is an integer from 0 to 2, preferably 0 or 1; and
p is an integer from 1 to 10, preferably 1 to 6;

with the proviso that the compound according to formula I is not:
Benzamide, N-[[5-[[[3-[[4-[(3-aminopropyl)amino]butyl] amino]propyl]amino]sulfonyl]-2-thienyl]methyl]; nor
Benzamide, N-[[5-[[[3-[[4-[(3-aminopropyl)amino] butyl] amino]propyl]amino]sulfonyl]-2-thienyl]methyl]-4-chloro]; nor
Benzamide,N,N'-[1,4-butanediylbis(imino-3,1-propanediyliminosulfonyl-5,2-thiophenediylmethylene)]bis [4-chloro].

In a second aspect, the invention provides a compound according to formula I without proviso for the treatment of disease.

In a third aspect, the invention provides a compound of formula I, without proviso, for the preparation of a pharmaceutical composition.

In a fourth aspect, the invention provides a compound according to formula I without proviso for the modulation of the JNK pathway.

In a fifth aspect, the invention provides a method of synthesis of a compound according to formula I with proviso.

DETAILED DESCRIPTION OF THE INVENTION

The following paragraphs provide definitions of various chemical moieties and terms, and are intended to apply uniformly throughout the specification and claims unless an otherwise expressly set out definition provides a different definition.

"C$_1$-C$_6$-alkyl" refers to monovalent branched or unbranched alkyl groups having 1 to 6 carbon atoms. This term is exemplified by groups such as methyl, ethyl, n-propyl, isopropyl, n-butyl, isobutyl, tert-butyl, n-hexyl and the like.

"C$_3$-C$_6$-cycloalkyl" refers to saturated or partially unsaturated carbocyclic rings having 3 to 6 carbon atoms. Examples include cyclopropyl, cyclobutyl, cyclopentyl, cyclohexyl, cyclohexenyl and the like.

"C$_3$-C$_6$-heterocycloalkyl" refers to saturated or partially unsaturated rings having 3 to 6 atoms and containing at least one heterotom selected from N, S and O. Examples include pyrrolidinyl, piperidinyl, piperazinyl, imidazolidinyl, morpholinyl and the like.

"Aryl" refers to unsaturated aromatic carbocyclic groups of from 6 to 14 carbon atoms having a single ring (e.g. phenyl) or multiple condensed rings (e.g. naphthyl). Examples include phenyl, naphthyl, phenanthrenyl and the like.

"Aryl C$_1$-C$_6$-alkyl" refers to C$_1$-C$_6$-alkyl groups, as defined above, having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1, 2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4, 3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"Heteroaryl C$_1$-C$_6$-alkyl" refers to C$_1$-C$_6$-alkyl groups having a heteroaryl substituent, including 2-furylmethyl, 2-thienylmethyl, 2-(1H-indol-3-yl)ethyl and the like.

"C$_2$-C$_6$ Alkenyl" refers to alkenyl groups preferably having from 2 to 6 carbon atoms and having at least 1 or 2 sites of alkenyl unsaturation. Examples include ethenyl (—CH═CH$_2$), n-2-propenyl (allyl, —CH$_2$CH═CH$_2$) and the like.

"Alkynyl" refers to alkynyl groups preferably having from 2 to 6 carbon atoms and having at least 1-2 sites of alkynyl unsaturation. Examples include ethynyl (—C≡CH), propargyl (—CH$_2$C≡CH), and the like.

"Acyl" refers to a group —C(O)R where R includes "C$_1$-C$_6$-alkyl", "aryl", "heteroaryl", "aryl C$_1$-C$_6$-alkyl" or "heteroaryl C$_1$-C$_6$-alkyl".

"Acyloxy" refers to a group —OC(O)R where R includes "C$_1$-C$_6$-alkyl", "aryl", "heteroaryl", "aryl C$_1$-C$_6$-alkyl" or "heteroaryl C$_1$-C$_6$-alkyl".

"Alkoxy" refers to a group —O—R where R includes "C$_1$-C$_6$-alkyl" or "aryl" or "hetero-aryl" or "aryl C$_1$-C$_6$-alkyl" or "heteroaryl C$_1$-C$_6$-alkyl". Preferred alkoxy groups include by way of example, methoxy, ethoxy, phenoxy and the like.

"Alkoxycarbonyl" refers to a group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl".

"Aminocarbonyl" refers to a group —C(O)NRR' where each R, R' is independently hydrogen or "$C_1$-$C_6$-alkyl" or "aryl" or "heteroaryl" or "aryl $C_1$-$C_6$-alkyl" or "heteroaryl $C_1$-$C_6$-alkyl".

"Acylamino" refers to a group —NR(CO)R' where each R, R' is independently hydrogen or "$C_1$-$C_6$-alkyl" or "aryl" or "heteroaryl" or "aryl $C_1$-$C_6$-alkyl" or "heteroaryl $C_1$-$C_6$-alkyl".

"Halogen" refers to fluoro, chloro, bromo and iodo atoms.

"Sulfonyl" refers to a group "—$SO_2$—R" wherein R is selected from H, "aryl", "heteroaryl", "$C_1$-$C_6$-alkyl", "$C_1$-$C_6$-alkyl" which may be substituted with halogens e.g. an —$SO_2$—$CF_3$ group, "aryl $C_1$-$C_6$-alkyl" or "heteroaryl $C_1$-$C_6$-alkyl".

"Sulfoxy" refers to a group "—S(O)—R" wherein R is selected from H, "$C_1$-$C_6$-alkyl", "$C_1$-$C_6$-alkyl" which may be substituted with halogens e.g. an —SO—$CF_3$ group, "aryl", "heteroaryl", "aryl $C_1$-$C_6$-alkyl" or "heteroaryl $C_1$-$C_6$-alkyl".

"Thioalkoxy" refers to groups —S—R where R includes "$C_1$-$C_6$-alkyl" or "aryl" or "heteroaryl" or "aryl $C_1$-$C_6$-alkyl" or "heteroaryl $C_1$-$C_6$-alkyl". Examples include thiomethoxy, thioethoxy, and the like.

"Substituted or unsubstituted": Unless otherwise constrained by the definition of the individual substituent, the above set out groups, like "alkyl", "Alkenyl", "alkynyl", "aryl" and "heteroaryl" etc. groups can optionally be substituted with from 1 to 5 substituents selected from the group consisting of "$C_1$-$C_6$-alkyl", "aryl $C_1$-$C_6$-alkyl", "heteroaryl $C_1$-$C_6$-alkyl", "$C_2$-$C_6$-alkenyl", "$C_2$-$C_6$-alkynyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or "complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salts of the formula —NR,R',R"+ Z−, wherein R, R', R" is independently hydrogen, alkyl, or benzyl, and Z is a counterion, including chloride, bromide, iodide, alkoxyde, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by a synthesis comprising an enantioselective step, whereby a surplus of one enantiomer in the order of at least about 52% ee is yielded. In the absence of an enantiomeric synthesis, racemic products are usually obtained that do however also have the inventive set out activity as JNKs inhibitors.

The present invention also includes the geometrical isomers, the optical active forms, enantiomers, diastereomers of compounds according to formula I mixtures of these, as well as their racemates and also pharmaceutically acceptable salts.

Preferred $Ar^1$ and $Ar^2$ in compounds according to formula I are those that are independently selected from the group consisting of phenyl, thienyl, furanyl, pyridyl, optionally substituted by substituted or unsubstituted $C_1$-$C_6$-alkyl, preferably trihalomethyl, substituted or unsubstituted $C_1$-$C_6$-alkoxy, substituted or unsubstituted $C_2$-$C_6$-alkenyl, substituted or unsubstituted $C_2$-$C_6$-alkynyl, amino, acylamino, aminocarbonyl, $C_1$-$C_6$-alkoxycarbonyl, aryl, carboxyl, cyano, halo, hydroxy, nitro, sulfonyl, sulfoxy, acyloxy and $C_1$-$C_6$-thioalkoxy. Most preferably, $Ar^1$ is a substituted phenyl, e.g. a halogenophenyl, hydroxyphenyl, alkoxy phenyl and most preferably $Ar^2$ is an unsubstituted or substituted thienyl or phenyl group.

A particularly preferred embodiment of the present invention is a sulfonamide derivative according to formula I, wherein $Ar^1$ is halogenophenyl, hydroxyphenyl, alkoxy phenyl, X is O, R' is hydrogen, m is 1, n is 0 or 1, p is 1 or 2, $Ar^2$ is thienylene or phenylene group, preferably a thienylene group and $R^a$, $R^{a'}$, $R^b$, $R^{b'}$ are hydrogen, $R^3$ is H, lower alkyl or aryl.

Another preferred group of compounds of the present invention includes those compounds of formula I, wherein $Ar^1$ is halogenophenyl, hydroxyphenyl, alkoxy phenyl, X is O, $R^1$ is hydrogen, m is 1, n is 0, 1 or 2, $Ar^2$ is thienylene or phenylene group, preferably a thienylene group, and either $R^a$ or $R^{a'}$ forms a 5-6 membered ring with $R^3$, or $R^a$ forms a 5-6 membered ring with $R^a$ and $R^3$ is H, lower alkyl or aryl.

In a further preferred group of compounds according to formula I, $Ar^1$ is 4-chlorophenyl, X is O, $R^1$ is hydrogen, m is 1, n is 0, 1 or 2, $Ar^2$ is thienylene or phenylene group, preferably a thienylene group, and $R^a$, $R^{a'}$, $R^b$, $R^{b'}$ are hydrogen, $R^3$ is H, lower alkyl or aryl and $R^4$ is H or $C_1$-$C_{10}$-alkyl or Aryl $C_1$-$C_{10}$-Alkyl, preferably hexyl or benzyl group.

Said aryl or heteroaryl groups may optionally be substituted by halogen, hydroxy, nitro, sulfonyl (e.g. trifluoromethylsulfonyl groups), $C_1$-$C_6$ alkyl or $C_1$-$C_6$ fluoroalkyl.

Compounds of formula I with proviso are believed to be novel and form an aspect of the invention.

Compounds of formula I, without proviso may be used for the treatment of a disease.

Specifically, the compounds of formula I are suitable for use in treating disorders of the immune system and neuronal system of mammals, notably of human beings. Such neuronal system disorders include for example neurodegenerative diseases e.g. Alzheimer's disease, Huntington's disease, Parkinson's disease, retinal diseases, spinal cord injury, multiple sclerosis, head trauma, epilepsy and seizures, ischemic and hemorragic brain strokes.

Immune system disorders include for example asthma, transplant rejection, inflammatory processes such as inflammatory bowel disease (IBD), cartilage and bone erosion disorders, rheumatoid arthritis, septic shock.

The compounds according to formula I are also suitable for use in treating cancers, such as breast, colorectal, pancreatic, prostate, testicular, ovarian, lung, liver and kidney cancers.

In another embodiment, the compounds according to formula I may be used for treating cardiovascular diseases including atherosclerosis, restenosis, stroke, ischemia, e.g. cerebral ischemia, myocordial infarction.

In another embodiment, the compounds according to formula I may be used for treating various ischemic conditions including heart and kidney failures, hepatic disorders and brain reperfusion injuries.

Preferably, the compounds according to formula I, alone or in the form of a pharmaceutical composition, are useful for the modulation of the JNK pathway, more specifically for treatment or prevention of disorders associated with expression or activity of JNK, notably of JNK2 and -3. Said modulation usually preferably involves the inhibition of the JNK pathways, notably of the JNK2 and/or -3. Such an abnormal expression or activity of JNK may be triggered by numerous stimuli (e.g. stress, septic shock, oxidative stress, cytokines) and may cause a cascade of processes, leading to, for example, uncontrolled apoptosis, inflammatory responses or oncogenic processes. These phenomena are frequently involved in various disorders including the above enumerated disorders and disease states. Hence, the compounds according to the invention may be used for the treatment of disorders by modulating the JNK function or signaling pathways. The modulation of the JNK function or pathways may involve its activation, but preferably it involves the down-regulation up to inhibition of the JNK pathways, notably of JNK1 and/or -2 and/or JNK3. The compounds of the invention may be employed alone or in combination with further pharmaceutical agents, e.g. with a further JNK modulator.

When employed as pharmaceuticals, the sulfonamide derivatives of the present invention are typically administered in the form of a pharmaceutical composition. Pharmaceutical compositions comprising a compound of formula I and a pharmaceutically acceptable carrier, diluent or excipient are also within the scope of the present invention. A person skilled in the art is aware of a whole variety of such carriers, diluents or excipients suitable to formulate a pharmaceutical composition.

The compounds according to formula I, together with a conventionally employed adjuvant, carrier, diluent or excipient may be formulated as pharmaceutical compositions and unit dosages, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfonamides derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the sulfonamide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the sulfonamide compound of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of (29).

The compounds of this invention can also be administered in sustained release forms or from sustained release drug delivery systems. A description of representative sustained release materials can also be found in the incorporated materials in (29).

Still a further object of the present invention is a process for preparing the sulfonamide derivatives according to formula I. The sulfonamides of this invention may be prepared from readily available starting materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvent used, but such conditions can be determined by one skilled in the art by routine optimization procedures.

SYNTHESIS OF COMPOUNDS OF THE INVENTION

The novel sulfonamide derivatives can be prepared from readily available starting materials. Three examples of synthetic pathways for the sulfonamides of formula I will be described.

The following abbreviations refer respectively to the definitions below:

AMEBA: (4-formyl-3-methoxyphenoxymethyl)polystyrene
Boc: Tert.butyloxy-carbonyl
DCE: Dichloroethane
DCM: Dichloromethane
DMA: Dimethylacetamide
DMF: Dimethylformamide
DMSO: Dimethylsulfoxide
EDTA: Ethylenediaminetetraacetic acid
Fmoc: Fluorenylmethyloxy-carbonyl NMP: N-methylpyrrolidone
TFA: Tri-Fluoro Acetic Acid
THF: Tetrahydrofuran
TLC: Thin Layer Chromatography
TMOF: Trimethylorthoformate Protocol I:

A preferred pathway starts with compounds of formula II wherein $R^a$, $R^{a'}$, $R^b$, $R^{b'}$, $R^2$, $R^3$, n and p are as defined for formula I and P is an amine protecting group.

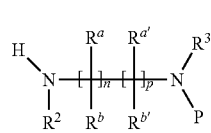

II

The mono-protected diamines of formula II are either known compounds, commercially available or they can be prepared from known compounds by conventional procedures. Typical examples of compounds of formula II comprise ethylenediamine, propylenediamine, (n- or t-)-butylenediamine, 1-amino-piperidine, aminomethylpiperidine.

In formula II typical amine protecting groups P are the following moieties: carbobenzoxy (Cbz), fluorenylmethyloxy-carbonyl (fmoc), allyloxycarbonyl, (2S)-2-([[1-(3,5-dimethoxyphenyl)-1-Methyl-ethoxy]-carbonyl], benzyl, 1,1,1-triphenylmethyl, most preferably tert.butyloxy-carbonyl (Boc). Other amine protecting groups will be known to the synthetic chemist (30).

Generally, such mono protected diamines are reacted with sulfonyl chlorides of formula III in the presence of a base as scavenger according to scheme I to lead to sulfonamides having the structure displayed in formula IV.

Scheme I:

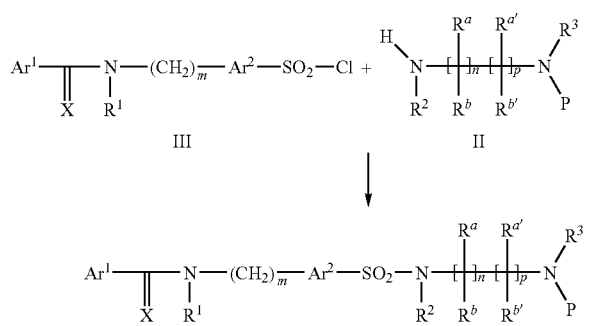

The above reaction may be conducted in the presence of a non-nucleophilic base such as triethylamine, di-isopropyl-ethylamine, potassium carbonate and the like in an aprotic solvent such as N,N-dimethyl-formamide, dimethylsulfoxide, N-methylpyrrolidone, acetonitrile, chloroform, dichloroethane or dichloromethane at a temperature from about 0° to about 100° C., preferably 20-60° C.

The sulfonyl chlorides of formula III used for the preparation of the sulfonamides of formula IV may be prepared using conventional sulfonylation methods using preferably chlorosulfonic acid as sulfonating reagent. Typically, the sulfonylation reaction is performed by treating the carboxamide of formula V with about 5 to about 10 molar equivalent of the sulfonating reagent in an inert solvent, such as dichloromethane, at a temperature ranging from about −70° C. to about 50° C.

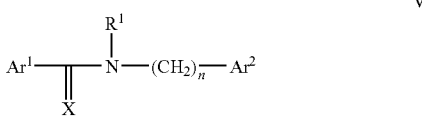

V

Preferably, the addition of chlorosulfonic acid takes place at −70° C. and leads to the formation of the intermediate sulfonic acid. Increasing the temperature to 20° C. allows the formation of the sulfonyl chloride of formula III. In those cases in which a mixture of sulfonated compounds is obtained, sulfonylchloride of formula III can be isolated by appropriate techniques such as flash chromatography or crystallisation.

Carboxamides of formula V (X=O) can be prepared by methods known to the skilled practitioner, for example by reaction of an amine (for example thien-2-yl methylamine, thien-2-yl ethylamine, furan-2-yl-methylamine or pyridyl-2-yl-methylamine) with an aroyl halide (for example 4-chloro-benzoylchloride, pyridinyl-benzoylchloride). Thiocarboxamides of formula V (X=S) can be obtained by methods known to the skilled practitioner, for example by treatment of a carboxamide of formula V with Lawesson's reagent (31).

Sulfonamide compounds of formula IV can also be obtained starting from mono-protected diamines of formula II, using solid phase methodologies, for example using polymer-bound reagents, such as polymer-bound triethylamine, di-isopropylethylamine, N-methylmorpholine, piperidine. Typically the sulfonylchloride of formula III is used in 1 to 5 equivalents excess of the corresponding monoprotected diamine of formula II. Ultimately the remaining excess of sulfonylchloride is trapped using polymer-bound primary amines such as amino-methyl polystyrene or trisamine. Pure sulfonamide is obtained upon filtration of the resins.

Subsequent removal of the protecting group, P, in the formula IV, using deprotection methods known in the art (30), leads to the primary or secondary amines of formula VI or the corresponding ammonium salt, depending on the applied deprotection protocol.

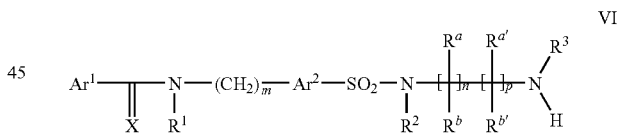

VI

The ammonium salt of the amine of formula VI may be neutralized in the presence of a base such as triethyl-amine, di-isopropylethylamine, or N-methylmorpholine. The alkylation of the amine moiety of formula VI into an amine of formula I is achieved via the reductive amination of an aldehyde or a ketone: the amine of formula VI is reacted with the desired aldehyde or ketone of formula VII wherein $R^5$ and $R^6$ are as defined for formula I.

VII

Typical examples of ketones and aldehydes of formula VII are $C_1$-$C_{10}$-aldehydes/ketones and ketones of the type Ph-C(O)—($C_1$-$C_6$)alkyl.

Depending whether the amine of formula VI is a primary or a secondary amine, a corresponding imine or iminium ion is preformed which may be isolated, or reduced in situ. In the case of primary amines as starting material, the intermediate imine may be isolated to avoid further alkylation. The imine intermediate is reduced with a suitable reducing agent such as sodium borohydride, sodium cyanoborohydride, hydrogen in the presence of Pd. A preferred reducing agent is sodium triacetoxy borohydride. Reduction of imines is favored when the imine is protonated, so the pH may be adjusted during reduction, for example by addition of acetic acid. Reductive amination is discussed in (32).

Sulfonamides of formula I can also be obtained from amines of formula VI or their ammonium salts using polymer-bound reagents. Polymer-bound base such as polymer-bound triethylamine, di-isopropylethylamine, N-methylmorpholine, piperidine may be used to neutralize the ammonium salt of amine VI. For the reductive amination, the appropriate aldehyde or ketone of formula VII may be used in 0.9 equivalents. Polymer-bound reducing agents such as polymer-bound sodium borohydride, sodium cyanoborohydride, sodium triacetoxy borohydride are used to reduce the intermediate imine to an amine of formula I. Excess amine of formula VI can be trapped using AMEBA aldehyde resin. Sulfonamides of formula I can then be obtained upon filtration of the resins.

Protocol II:

Another preferred pathway starts with compounds of formula VIII wherein $R^a$, $R^{a'}$, $R^b$, $R^{b'}$, $R^2$, $R^3$, n and p are as defined for formula I, and P is an amine protecting group. The mono-protected diamines of formula VIII are either known compounds, commercially available or they can be prepared from known compounds by conventional procedures.

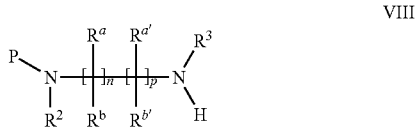

VIII

In formula VIII, the typical amine protecting groups, P, may be selected from the following moieties: carbobenzoxy (Cbz), fluorenylmethyloxy-carbonyl (fmoc), allyloxycarbonyl, (2S)-2-([[1-(3,5-dimethoxyphenyl)-1-methylethoxy]-carbonyl], benzyl, 1,1,1-triphenylmethyl, most preferably tert.butyloxy-carbonyl (30). Other amine protecting groups will be known for the synthetic chemist (30).

Alkylation of the amine of formula VIII is achieved via the reaction with an aldehyde or a ketone of formula VII through reductive amination, leading to an amine of formula IX as follows:

Scheme II:

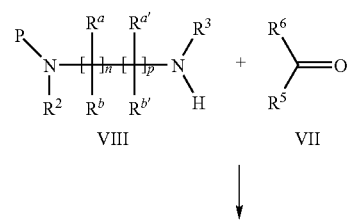

VIII        VII

-continued

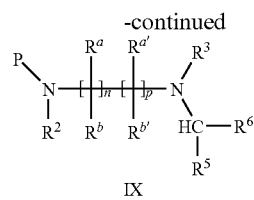

IX

The amine of formula VIII is reacted with the appropriate aldehyde or ketone of formula VII, if necessary in the presence of a non nucleophilic base such as triethylamine, di-isopropylethylamine, or N-methylmorpholine to ensure some of the amine is deprotonated, in an polar solvent such as DCE, THF, TMOF, DMF, DMA, DCM, methanol, NMP. The intermediate imine derivative may be reduced in situ or isolated upon evaporating the solvent, and reduced in a separate reaction. In the case of primary amines as starting material, the intermediate imine may be isolated to avoid further alkylation. Reduction of imines is favored when the imine is protonated, so the pH may be adjusted during reduction, for example by addition of acetic acid. Reduction of the imine derivative is performed with a suitable reducing agent such as sodium borohydride, sodium cyanoborohydride, hydrogen in the presence of Pd, most preferably sodium triacetoxy borohydride. Preferred solvents are DCE, THF, TMOF, DMF, DMA, DCM, methanol, NMP.

Amines of formula IX can also be obtained via solid phase synthesis using polymer-bound reagents. Polymer-bound reducing agents such as polymer-bound sodium borohydride, sodium cyanoborohydride, sodium triacetoxy borohydride are used to reduce the imine to the corresponding amine of formula IX. Excess of amine VIII can be removed using AMEBA aldehyde resin. Amines of formula VIII can then be obtained upon filtration of the resins.

Subsequent removal of the protecting group P in formula IX, using deprotection methods known to the skilled practitioner, as mentioned above, leads to the corresponding amine X.

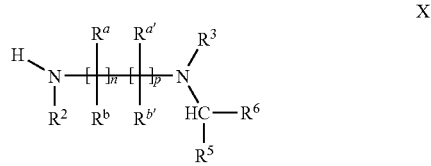

X

Amine X may be obtained as the corresponding ammonium salt depending on the applied deprotection technique used.

Ultimately, such amines or ammonium salts are reacted with sulfonylchlorides of formula III in the presence of a base as scavenger to obtain sulfonamides shown in formula I.

The reaction is generally conducted in the presence of a non-nucleophilic base such as triethylamine, diisopropyl-ethylamine, potassium carbonate and the like in an aprotic solvent such as N,N-dimethyl-formamide, dimethylsulfoxide, N-methylpyrrolidone, acetonitrile, chloroform, dichloroethane or dichloromethane at a temperature from about 0° to about 100° C., preferably 20-60° C. In case of ammonium salts of formula X the reaction should be performed in excess of scavenger base.

Sulfonamide I can also be synthesised via a solid phase synthesis route using polymer-bound reagents, such as polymer-bound triethylamine, di-isopropylethylamine, N-methylmorpholine, piperidine, carbonate. Typically the sulfonylchloride III is used in 1. to 1.5 equivalents excess of the corresponding amine VIII. Ultimately the remaining excess of sulfonylchloride is trapped using polymer-bound primary amines such as aminomethyl polystyrene or trisamine. Pure sulfonamide I is obtained upon filtration of the resins.

In the case of compounds of formula I where $R^4$ is H, the mode of synthesis could follow the protocol I and the process would stop once the compound VI is formed. Compounds of formula VI then represent a subset of compounds of formula I.

For the formation of compounds of formula I wherein $R^3$ is an aromatic moiety, Protocol III should be used.

Protocol III:

A sulfonyl chloride of formula III is reacted with an aminoalcohol of formula XI to obtain an alcohol of formula XII. The reaction is conducted in a polar solvent such as DMF or THF. Any excess of amine is extracted into an acidic aqueous phase After solvent evaporation, the alcohol of formula XII is submitted to oxidation with an oxidizing agent e.g. pyridine N-oxide to yield to an aldehyde of formula XIII.

The aldehyde of formula XIII is subjected to a reductive amination such as already described in Protocol I or II. In this case, an aldehyde of formula XIII is reacted with an aromatic amine of formula XIV in an polar solvent such as DCE, THF, TMOF, DMF, DMA, DCM, methanol, NMP to lead to an amine of formula I. The intermediate imine may be reduced in situ or isolated upon evaporating the solvent, and reduced in a separate reaction. Formation of the inline may be favored by adjusting the pH to mildly acidic to neutral, for example, by addition of acetic acid or if necessary a small quantity of base. Reduction of the imine derivative is performed with a suitable reducing agent such as sodium borohydride, sodium cyanoborohydride, hydrogen in the presence of Pd, most preferably sodium triacetoxy borohydride. Preferred solvents are DCE, THF, TMOF, DMF, DMA, DCM, methanol, NMP.

Scheme III:

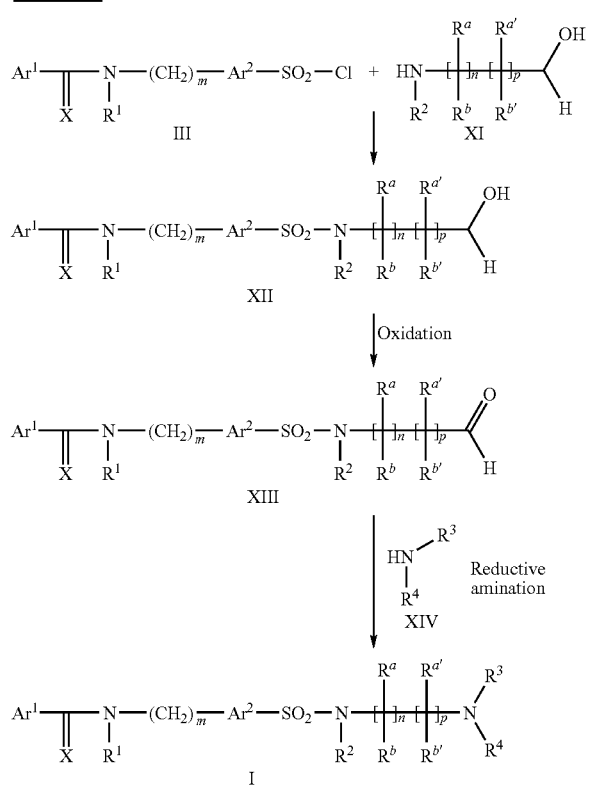

If the above set out general synthetic methods are not applicable for obtaining certain compounds of formula I, suitable methods of preparation known by a person skilled in the art should be used.

EXAMPLES

The invention will be illustrated by means of the following examples which are not to be construed as limiting the scope of the invention.

The compounds of the present invention may be synthesized according to the different synthesis pathways provided above. The following examples illustrate preferred methods for synthesizing the compounds according to formula I and determining their activities.

Example I 5-({[1-(4-Chloro-phenyl)-methanoyl]-amino}-methyl)-thiophene-2-sulfonyl chloride (1b) (compound of formula III)

a) 4-Chloro-N-thiophen-2-ylmethyl-benzamide (1a)

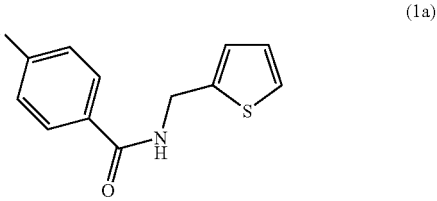

(1a)

A solution of 4-chlorobenzoyl chloride (0.114 mol) in 50 mL dry $CH_2Cl_2$ was added over 30 min to a stirred solution of 2-aminomethyl-thiophene (0.137 mol) and $^iPr_2NEt$ (0.25 mol) in $CH_2Cl_2$ (200 mL) at 0° C. A white solid was formed and the reaction was allowed to warm to room temperature over 1 h. The mixture was diluted with 200 mL of $CH_2Cl_2$, washed twice with HCl aq. (0.1N) and dried over $MgSO_4$. Evaporation of the solvents afforded 28 g (98%) of the title benzamide (1a) as a white solid: m.p. 153-54° C., $^1H$ NMR ($CDCl_3$) δ 7.9 (d, J=8.67 Hz, 2H), 7.58 (d, J=8.67 Hz, 2H), 7.44 (dd, J=3.77, 1.13 Hz, 1H), 7.22 (d, J=5.27 Hz, 1H), 7.16 (dd, J=3.39, 5.27 Hz, 1H), 6.62 (br d, 1H), 4.98 (d, J=5.65 Hz, 2H).

b) 5-({[1-(4-Chloro-phenyl)-methanoyl]-amino}-methyl)-thiophene-2-sulfonyl chloride (1b)

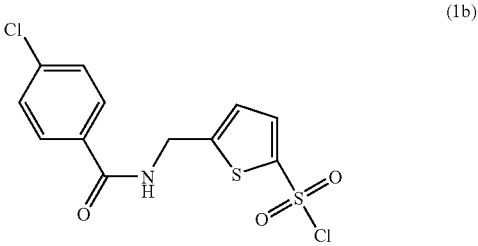

(1b)

Chlorosulfonic acid (20.1 mL, 198 mmol) in $CH_2Cl_2$ (80 mL) was added dropwise to a solution of the above compound (1a) (10 g, 40 mmol) in $CH_2Cl_2$ (500 mL) at −80° C. The mixture was allowed to reach room temperature in 5 h. The reaction mixture was poured on ice and quickly extracted with $CH_2Cl_2$. The organic layer was dried over $MgSO_4$ and the solvent was evaporated to dryness which afforded 8.8 g (63%) of desired sulfonyl chloride (1b); mp 133-35° C., $^1H$ NMR DMSO-d6) δ 9.21 (t, J=6.4 Hz, 1H), 7.87 (d, J=8.67 Hz, 2H), 7.53 (d, J=8.67 Hz, 2H), 6.91 (d, J=3.39 Hz, 1H), 6.77 (d, J=3.39 Hz, 1H), 4.53 (d, J=3.77 Hz, 2H).

Example II

4-Chloro-N-{5-[1-(4-trifluoromethyl-benzyl)-piperidin-3-ylsulfamoyl]-thiophen-2-ylmethyl}-benzamide (2)

The synthesis of the above compound (2) is a 3-step-synthesis (see scheme I).

(2)

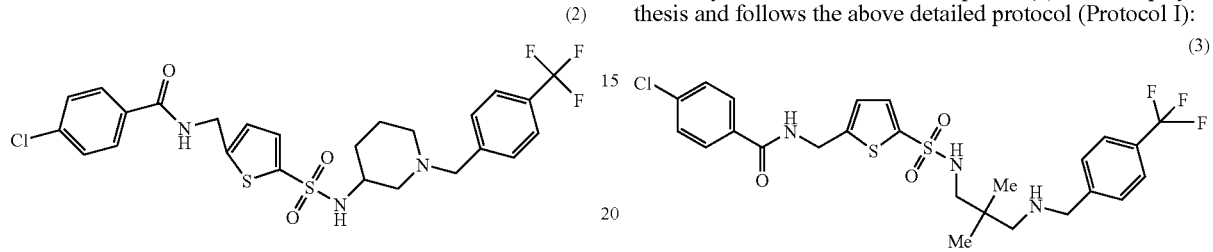

Protocol I:

Step 1—N-sulfonylation (Compound of Formula IV)

The mono protected diamine (+/−)-3-Amino-1-N-Boc-Piperidine (compound of formula II) (0.4 g, 2 mMol, 1 eq), 5-(4-chlorobenzamidomethyl) thiophene-2-sulphonyl chloride (1b) (compound of formula III) (0.99 g, 2.4 mMol, 1.2 eq), and piperidine resin (2 g, 1.5 eq, loading of 1.5 mMol/g) are swirled in THF (50 ml) on orbital shaker overnight. Aminomethyl polystyrene (1.82 g, 1 eq, loading of 1.1 mMol/g) is added to the flask and contents swirled on orbital shaker overnight.

The resins are filtered and washed with a further 50 ml of THF. Filtrates are combined and solvent is evaporated under reduced pressure to yield quantitatively the corresponding sulfonamide (formula IV). No further purification is required at this stage.

Step 2—Removal of N-Boc-Protection (Compound of Formula VI):

The sulfonamide from Step 1 is loaded into a round bottomed flask and dissolved in 50% TFA/DCM (50 ml). The flask is swirled on orbital shaker until completion of the reaction is confirmed by TLC.

The solvent is evaporated under reduced pressure to yield TFA ammonium salt. The salt dissolved in methanol (50 ml), Carbonate resin (2.67 g, 2 eq, loading of 1.5 mMol/g) is added and the contents are swirled on orbital shaker over night. The resin is filtered and washed with a further 50 ml of methanol. Filtrates are combined and the solvent is evaporated under reduced pressure to yield quantitatively the free amine. No purification is required at this stage.

Step 3—Reductive Amination (Compound of Formula I)

A round bottomed flask is charged with the free amine from Step 2 (0.41 g, 1 mMol, 1 eq), the aldehyde 4-(Trifluoromethyl)-Benzaldehyde (0.16 g, 0.9 mMol, 0.9 eq), and glacial acetic acid (60 μl, 1 mMol, 1 eq). Methanol (30 ml) is added and the flask is swirled on orbital shaker overnight.

Borohydride resin (0.67 g, 2 eq, loading of 2.5 mMol/g) is added to flask and contents are swirled on orbital shaker overnight.

AMEBA (aldehyde) resin (0.46 g, 0.5 eq, loading of 0.9 mMol/g) is added to flask and contents swirled on orbital shaker overnight.

The resins are filtered off and washed with a further 30 ml of methanol, and filtrates are combined and solvent is evaporated under reduced pressure to yield the crude product. The crude product is purified by preparative HPLC using acetonitrile and water as eluents to obtain the pure 4-Chloro-N-{5-[1-(4-trifluoromethyl-benzyl)-piperidin-3-ylsulfamoyl]-thiophen-2-ylmethyl}-benzamide (2).

Example III

4-Chloro-N-{5-[2,2-dimethyl-3-(4-trifluoromethyl-benzylamino)-propylsulfamoyl]-thiophen-2-ylmethyl}-benzamide (3)

The synthesis of the above compound (3) is a 3-step-synthesis and follows the above detailed protocol (Protocol I):

(3)

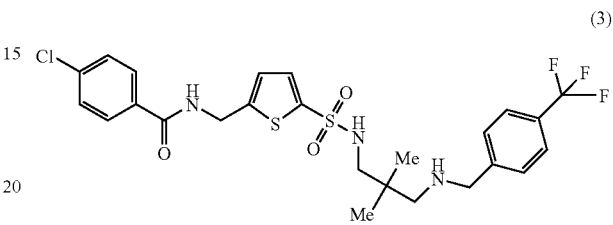

Step 1—N-sulfonylation (Compound of Formula IV)

In this case the mono-protected diamine used is the 1-Boc-Amino-2,2-Dimethyl-1,3-Propanediamine.

Step 2—Removal of N-Boc-Protection (Compound of Formula VI):

The sulfonamide obtained through the above step 1 is N-Boc deprotected to give the corresponding free amine.

Step 3—Reductive Amination (Compound of Formula I)

The free amine obtained through the above step 2 is reacted in this case with 4-(Trifluoromethyl)-Benzaldehyde. The final product after purification is 4-Chloro-N-{5-[2,2-dimethyl-3-(4-trifluoromethyl-benzylamino)-propylsulfamoyl]-thiophen-2-ylmethyl}-benzamide (3).

Example IV

4-Chloro-N-(5-{3-[methyl-(4-trifluoromethyl-benzyl)-amino]-propylsulfamoyl}-thiophen-2-ylmethyl)-benzamide (4)

The synthesis of the above compound (4) is a 3-step-synthesis and follows the above detailed protocol (Protocol I):

(4)

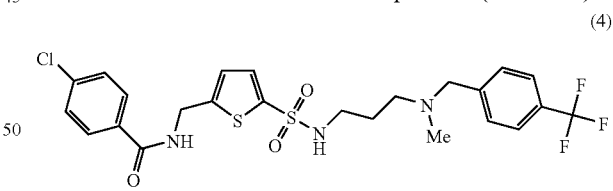

Step 1—N-sulfonylation (Compound of Formula I)

In this case the mono-protected diamine used is the N-(3-Aminopropyl)-N-Methylcarbamic Acid Tert-Butyl Ester.

Step 2—Removal of N-Boc-protection (Compound of Formula VI):

The sulfonamide obtained through the above step 1 is N-Boc deprotected to give the corresponding free amine.

Step 3—Reductive Amination (Compound of Formula I)

The free amine obtained through the above step 2 is reacted in this case with 4-(Trifluoromethyl)-Benzaldehyde. The final product after purification is 4-Chloro-N-(5-{3-[methyl-(4-trifluoromethyl-benzyl)-amino]-propylsulfamoyl}-thiophen-2-ylmethyl)-benzamide (4).

Example V

4-Chloro-N-{5-[3-(hexyl-methyl-amino)-proylsulfamoyl]-thiophen-2-ylmethyl}-benzamide (5)

The synthesis of the above compound (5) is a 3-step-synthesis and follows the above detailed protocol (Protocol I):

(5)

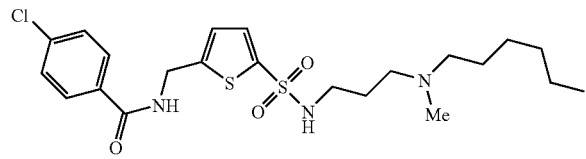

Step 1—N-sulfonylation (Compound of Formula IV)
In this case the monoBoc diamine used is the N-(3-Aminopropyl)-N-Methylcarbamic Acid Tert-Butyl Ester.

Step 2—Removal of N-Boc-Protection (Compound of Formula VI):
The sulfonamide obtained through the above step 1 is N-Boc deprotected to give the corresponding free amine.

Step 3—Reductive Amination (Compound of Formula ):
The free amine obtained through the above step 2 is reacted in this case with 1-Hexanal. The final product after purification is 4-Chloro-N-{5-[3-(hexyl-methyl-amino)-propylsulfamoyl]-thiophen-2-ylmethyl}-benzamide (5).

Example VI

4-Chloro-N-{5-[2-(4-trifluoromethyl-benzylamino)-cyclohexylsulfamoyl]-thiophen-2-ylmethyl}-benzamide (6)

The synthesis of the above compound (6) is a 3-step-synthesis and follows the above detailed protocol (Protocol I):

(6)

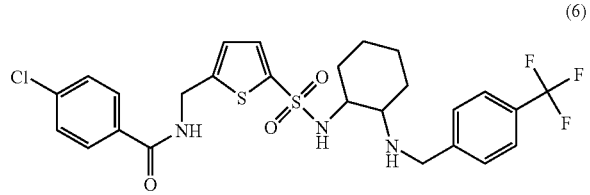

Step 1—N-sulfonylation (Compound of Formula IV)
In this case the mono-protected diamine used is the 1-Boc-Amino-2-Aminocyclohexane.

Step 2—Removal of N-Boc-Protection (Compound of Formula VI):
The sulfonamide obtained through the above step 1 is N-Boc deprotected to give the corresponding free amine.

Step 3—Reductive Amination (Compound of Formula I)
The free amine obtained through the above step 2 is reacted in this case with 4-(Trifluoromethyl)-Benzaldehyde. The final product after purification is of 4-Chloro-N-{5-[2-(4-trifluoromethyl-benzylamino)-cyclohexylsulfamoyl]-thiophen-2-ylmethyl}-benzamide (6).

Example VII

4-Chloro-N-[5-(2-hexylamino-ethylsulfamoyl)-thiophen-2-ylmethyl]-benzamide (7)

The synthesis of the above compound (7) is a 3-step-synthesis and follows the above detailed protocol (Protocol I):

(7)

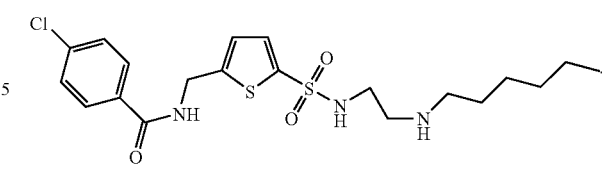

Step 1—Sulfonylation (Compound of Formula IV)
In this case the mono-protected diamine used is the 1-Boc-Amino-Ethylenediamine.

Step 2—Removal of N-Boc-Protection (Compound of Formula (VI):
The sulfonamide obtained through the above step 1 is N-Boc deprotected to give the corresponding free amine.

Step 3—Reductive Amination (Compound of Formula I)
The free amine obtained through the above step 2 is reacted in this case with 1-Hexanal. The final product after purification is 4-Chloro-N-[5-(2-hexylamino-ethylsulfamoyl)-thiophen-2-ylmethyl]-benzamide (7).

Example VIII

4-Chloro-N-{5-[1-(4-trifluoromethyl-benzyl)-piperidin-4-ylsulfamoyl]-thiophen-2-ylmethyl}-benzamide (8)

The synthesis of the above compound (8) is a 3-step-synthesis and follows the above detailed protocol (Protocol I):

(8)

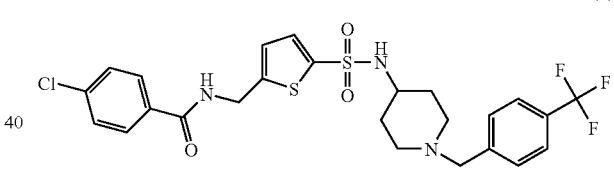

Step 1—Sulfonamide Formation (Compound of Formula IV)
In this case the mono-protected diamine used is the 4-Amino-1-Boc-Piperidine.

Step 2—Removal of N-Boc-Protection (Compound of Formula VI)
The sulfonamide obtained through the above step 1 is N-Boc deprotected to give the corresponding free amine.

Step 3—Reductive Amination (Compound of Formula I)
The free amine obtained through the above step 2 is reacted in this case with 4-(Trifluoromethyl)-Benzaldehyde. The final product after purification is 4-Chloro-N-{5-[1-(4-trifluoromethyl-benzyl)-piperidin-4-ylsulfamoyl]-thiophen-2-ylmethyl}-benzamide (8).

Example IX

4-Chloro-N-[5-(3-hexylamino-2,2-dimethyl propylsulfamoyl)-thiophen-2-ylmethyl]-benzamide (9)

The synthesis of the above compound (9) is a 3-step-synthesis and follows the above detailed protocol (Protocol I):

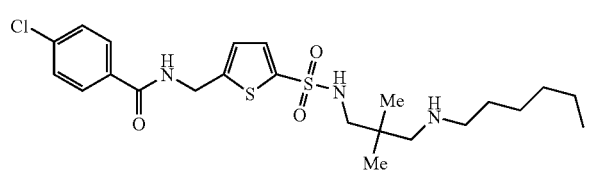

(9)

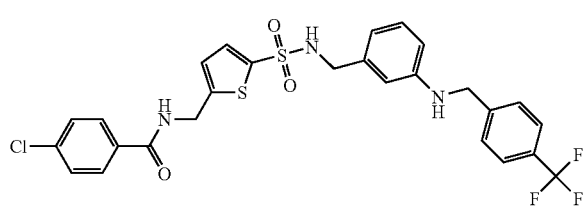

(10)

Step 1—Sulfonylation (Compound of Formula IV)
In this case the mono-protected diamine used is the 1-Boc-Amino-2,2-Dimethyl-1,3-Propanediamine.

Step 2—Removal of N-Boc-Protection (Compound of Formula VI):
The sulfonamide obtained through the above step 1 is N-Boc deprotected to give the corresponding free amine.

Step 3—Reductive Amination (Compound of Formula I)
The free amine obtained through the above step 2 is reacted in this case with 1-Hexanal. The final product after purification is 4-Chloro-N-[5-(3-hexylamino-2,2-dimethyl propylsulfamoyl)-thiophen-2-ylmethyl]-benzamide (9).

Example X

4-Chloro-N-{5-[3-(4-trifluoromethyl-benzylamino)-benzylsulfamoyl]-thiophen-2-ylmethyl}-benzamide (10)

The synthesis of the above compound (10) is a 3-step-synthesis and follows the above detailed protocol (Protocol I):

Step 1—Sulfonylation (Compound of Formula IV)
In this case the mono-protected diamine used is 3-(aminomethyl)-1-N-Boc-aniline Step 2—Removal of N-Boc-Protection (Compound of Formula VI:
The sulfonamide obtained through the above step 1 is N-Boc deprotected to give the corresponding free amine.

Step 3—Reductive Amination (Compound of Formula I)
The free amine obtained through the above step 2 is reacted in this case with 4-(Trifluoromethyl)-Benzaldehyde. The final product after purification is 4-Chloro-N-{5-[3-(4-trifluoromethyl-benzylamino)-benzylsulfamoyl]-thiophen-2-ylmethyl}-benzamide (10).

The following compounds were prepared on a parallel fashion according to the generic procedure (Protocol I) described above.

The following table provides HPLC data and mass spectroscopy data of the mentioned examples [1],[2].

| Example | Name | HPLC[1] (Rt mn) | Mass[2] M + 1 | Mass[2] M − 1 |
|---|---|---|---|---|
| 2 | 4-Chloro-N-{5-[1-(4-trifluoromethyl-benzyl)-piperidin-3-ylsulfamoyl]-thiophen-2-ylmethyl}-benzamide | 4.91 | 572 | 570 |
| 3 | 4-Chloro-N-{5-[2,2-dimethyl-3-(4-trifluoromethyl-benzylamino)-propylsulfamoyl]-thiophen-2-ylmethyl}-benzamide | 3.77 | 574 | 572 |
| 4 | 4-Chloro-N-(5-{3-[methyl-(4-trifluoromethyl-benzyl)-amino]-propylsulfamoyl}-thiophen-2-ylmethyl)-benzamide | 3.62 | 560 | 558 |
| 5 | 4-Chloro-N-{5-[3-(hexyl-methyl-amino)-propylsulfamoyl]-thiophen-2-ylmethyl}-benzamide | 3.48 | 486 | 484 |
| 6 | 4-Chloro-N-{5-[2-(4-trifluoromethyl-benzylamino)-cyclohexylsulfamoyl]-thiophen-2-yhnethyl}-benzamide | 3.78 | 586 | 584 |
| 7 | 4-Chloro-N-[5-(2-hexylamino-ethylsulfamoyl)-thiophen-2-ylmethyl]-benzamide | 3.38 | 458.1 | 456 |
| 8 | 4-Chloro-N-{5-[1-(4-trifluoromethyl-benzyl)-piperidin-4-ylsulfamoyl]-thiophen-2-ylmethyl}-benzamide | 3.62 | 572 | 570 |
| 9 | 4-Chloro-N-[5-(3-hexylamino-2,2-dimethyl-propylsulfamoyl)-thiophen-2-ylmethyl]-benzamide | 3.68 | 500 | 498 |
| 10 | 4-Chloro-N-{5-[3-(4-trifluoromethyl-benzylamino)-benzylsulfamoyl]-thiophen-2-ylmethyl}-benzamide | 5.83 | 594 | 592 |

[1] HPLC conditions: C8 Symmetry a-MeCN, 0.09% TFA, 0 to 100% (8 min)
[2] Mass spectrum APCI

Example XI

4-Chloro-N-{5-[3-(4-trifluoromethyl-benzylamino)-propylsulfamoyl]-thiophen-2-ylmethyl}-benzamide (11)

The synthesis of the above compound (11) is a 3-step-synthesis and follows the below detailed protocol (Protocol II):

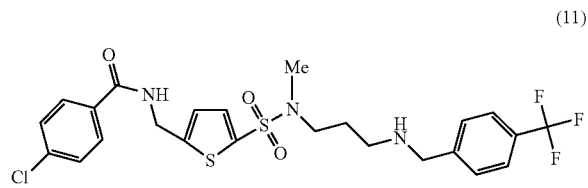

(11)

Protocol II:

Step 1—Reductive Amination (Compound of Formula IX)

A round bottomed flask is charged with the mono-protected diamine (compound of formula VIII), N-(3-Aminopropyl)-N-Methylcarbamic Acid Tert-Butyl Ester, (1 mMol, 1 eq), an aldehyde of formula VII, 4-(Trifluoromethyl)-Benzaldehyde (0.9 mMol, 0.9 eq), and glacial acetic acid (60 µl, 1 mMol, 1 eq). Methanol (30 ml) is added and the flask is swirled on an orbital shaker overnight.

Borohydride resin (0.67 g, 2 eq, loading of 2.5 mMol/g) is added to the flask and the contents are swirled on orbital shaker overnight.

AMEBA (aldehyde) resin (0.46 g, 0.5 eq, loading of 0.9 mMol/g) is added to flask and contents are swirled on an orbital shaker overnight.

All resins are filtered and washed with a further 30 ml of Methanol, filtrates are combined and the solvent is evaporated under reduced pressure to yield product. The resulting 3-Boc-Aminomethyl-Piperidine alkylated amine (compound of formula IX) is used without purification for further reactions.

Step 2—Removal of N-Boc-Protection (Compound of Formula X)

The mono-protected mono-alkyl diamine obtained in Step 1 is loaded into a 100 ml round bottomed flask and dissolved in 50% TFA/DCM (50 ml). The flask is swirled on an orbital shaker until the reaction is complete as checked by TLC.

The solvent is evaporated under reduced pressure to yield the TFA ammonium salt.

The salt is dissolved in Methanol (50 ml), Carbonate resin (2.67 g, 2 eq, loading of 1.5 mMol/g) is added to the flask and the contents are swirled on an orbital shaker overnight.

The resin is filtered and washed with further 50 ml Methanol. Combined filtrates are evaporated under reduced pressure to yield the free monoalkyl diamine (formula X). No purification is required at this stage.

Step 3—N-Sulfonylation (Compound of Formula I)

A round bottomed flask is charged with the monoalkyl-diamine obtained from Step 2 (0.25 g, mMol, 1 eq), 5-(4-chlorobenzamidomethyl) thiophene-2-sulphonyl chloride, (1b) (0.42 g, 1.2 mMol, 1.2 eq), and piperidine resin (1 g, 1.5 eq, loading of 1.5 mMol/g) in THF (50 ml). The flask is swirled on an orbital shaker overnight.

Aminomethyl polystyrene (0.91 g, 1 eq, loading of 1.1 mMol/g) is added to the flask and the contents are swirled on orbital shaker overnight.

The resins are filtered off and washed with a further 50 ml of THF. Filtrates are combined and solvent is evaporated under reduced pressure to yield crude product. The crude product is purified by preparative HPLC using Acetonitrile and water as eluents leading to compound (11), 4-Chloro-N-{5-[3-(4-trifluoromethyl-benzylamino)-propylsulfamoyl]-thiophen-2-ylmethyl}-benzamide.

Example XII

4-Chloro-N-(5-{[1-(4-trifluoromethyl-benzyl)-piperidin-3-ylmethyl]-sulfamoyl}-thiophen-2-ylmethyl)-benzamide (12)

The synthesis of the above compound (12) is a 3-step-synthesis and consists in the above detailed protocol (see scheme 11):

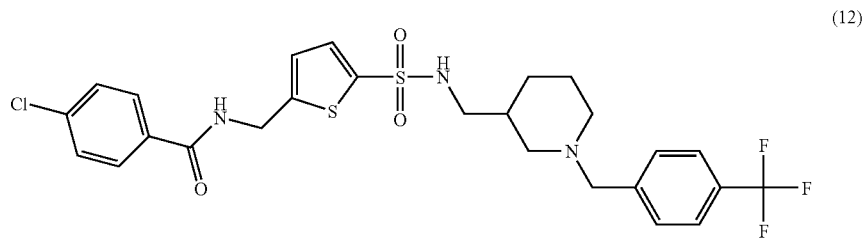

(12)

Step 1—Reductive Amination (Compound of Formula (IX)
The mono-protected diamine used is 3-Boc-Aminomethyl-Piperidine and the aldehyde is 4-(Trifluoromethyl)-Benzaldehyde.

Step 2—Removal of N-Boc-Protection (Compound of Formula (X)
The mono-protected mono-alkyl diamine obtained in Step 1 is deprotected to obtain the corresponding free amine.

Step 3—N-Sulfonylation (Compound of Formula I)
The free amine from step 2 is reacted with compound (1b) to yield to compound (12), 4-Chloro-N-(5-{[1-(4-trifluoromethyl-benzyl)-piperidin-3-ylmethyl]-sulfamoyl}-thiophen-2-ylmethyl)-benzamide.

Example XIII

4-Chloro-N-(5-{methyl-[3-(4-trifluoromethyl-benzylamino)-propyl]-sulfamoyl}-thiophen-2-ylmethyl)-benzamide (13)

The synthesis of the above compound (12) is a 3-step-synthesis and follows the above detailed protocol (Protocol II):

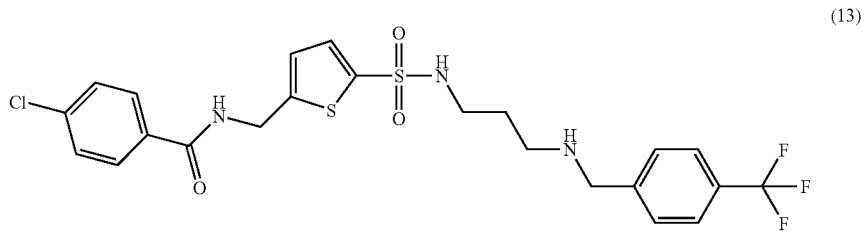

(13)

Step 1—Reductive Amination (Compound of Formula (IX)
The mono-protected diamine used is 1-Boc-Amino-1,3-Propanediamine and the aldehyde is 4-(Trifluoromethyl)-Benzaldehyde.

Step 2—Removal of N-Boc-Protection (Compound of Formula X)
The mono-protected mono-alkyl diamine obtained in Step 1 is deprotected to obtain the corresponding free amine.

Step 3—N-Sulfonylation (Compound of Formula I)
The free amine from step 2 is reacted with compound (1b) to yield to 4-Chloro-N-(5-{methyl-[3-(4-trifluoromethyl-benzylamino)-propyl]-sulfamoyl}-thiophen-2-ylmethyl)-benzamide (13).

Example XIV

4-Chloro-N-{5-[(3-hexylamino-propyl)-methyl-sulfamoyl]-thiophen-2-ylmethyl}-benzamide (14)

The synthesis of the above compound (14) is a 3-step-synthesis and follows the above detailed protocol (Protocol II):

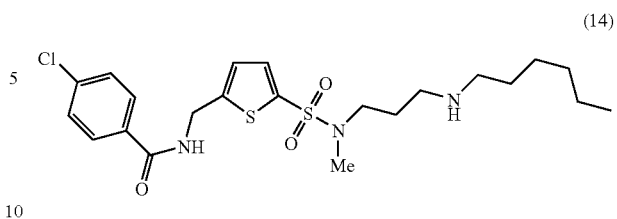

(14)

Step 1—Reductive Amination (Compound of Formula IX)
The mono-protected diamine used is N-(3-Aminopropyl)-N-Methylcarbamic Acid Tert-Butyl Ester and the aldehyde is 1-Hexanal.

Step 2—Removal of N-Boc-Protection (Compound of Formula X)
The mono-protected mono-alkyl diamine obtained Step 1 is deprotected to obtain the corresponding free amine.

Step 3—N-Sulfonylation (Compound of Formula I)
The resulting free amine from step 2 is reacted with compound (1b) to yield to 4-Chloro-N-{5-[(3-hexylamino-propyl)-methyl-sulfamoyl]-thiophen-2-ylmethyl}-benzamide (14).

Example XV

4-Chloro-N-(5-{[1-(4-trifluoromethyl-benzyl)-pyrrolidin-2-ylmethyl]-sulfamoyl}-thiophen-2-ylmethyl)-benzamide (15)

The synthesis of the above compound (15) is a 3-step-synthesis and follows the above detailed protocol (Protocol II):

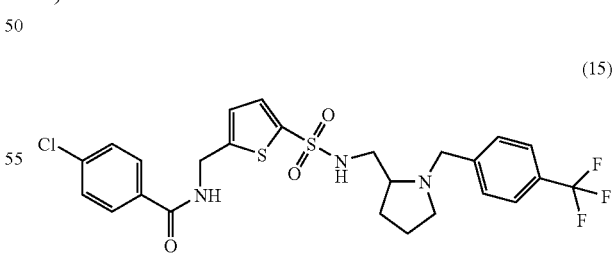

(15)

Step 1—Reductive Amination (Compound of Formula IX)
The mono-protected diamine used is 2-(N-Tert-Butoxycarbonylaminomethyl)-Pyrrolidine and the aldehyde is 4-(Trifluoromethyl)-Benzaldehyde.

Step 2—Removal of N-Boc-Protection (Compound of Formula X)

The mono-protected mono-alkyl diamine obtained in Step 1 is deprotected to obtain the corresponding free amine.

Step 3—N-Sulfonation (Compound of Formula I)

The resulting free amine from step 2 is reacted with compound (1b) to yield to 4-Chloro-N-(5-{[1-(4-trifluoromethyl-benzyl)-pyrrolidin-2-ylmethyl]-sulfamoyl}-thiophen-2-yl-methyl)-benzamide (15).

The following compounds were prepared according to the generic procedure (protocol II) described above The following table provides HPLC data and mass spectroscopy data of the mentioned examples [1],[2].

| Example | Name | HPLC[1] (Rt mn) | Mass[2] M + 1 | Mass[2] M − 1 |
|---|---|---|---|---|
| 11 | 4-Chloro-N-{5-[3-(4-trifluoromethyl-benzylamino)-propylsulfamoyl]-thiophen-2-ylmethyl}-benzamide | 3.58 | 546 | 544 |
| 12 | 4-Chloro-N-(5-{[1-(4-trifluoromethyl-benzyl)-piperidin-3-ylmethyl]-sulfamoyl}-thiophen-2-ylmethyl)-benzamide | 3.69 | 586 | 584 |
| 13 | 4-Chloro-N-(5-{methyl-[3-(4-trifluoromethyl-benzylamino)-propyl]-sulfamoyl}-thiophen-2-ylmethyl)-benzamide | 3.78 | 560 | 558 |
| 14 | 4-Chloro-N-{5-[(3-hexylamino-propyl)-methyl-sulfamoyl]-thiophen-2-ylmethyl}-benzamide | 3.65 | 486 | 484 |
| 15 | 4-Chloro-N-(5-{[1-(4-trifluoromethyl-benzyl)-pyrrolidin-2-ylmethyl]-sulfamoyl}-thiophen-2-ylmethyl)-benzamide | 3.6 | 572 | 570 |

[1]HPLC conditions: C8 Symmetry a-MeCN, 0.09% TFA, 0 to 100% (8 min)
[2]Mass spectrum APCI

Example XVI

4-Chloro-N-{5-[2,2-dimethyl-3-(3-trifluoromethane-sulfonyl-phenylamino)-propylsulfamoyl]-thiophen-2-ylmethyl}-benzamide (16)

The synthesis of the above compound (16) is a 3-step-synthesis and consists of the following protocol (see scheme III):

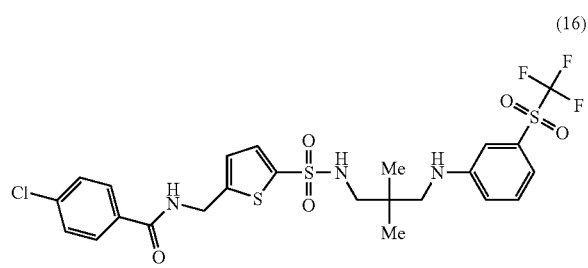

(16)

Step 1—Sulfonylation of an Aminoalcohol (Compound of Formula XII)

To a stirred solution of 2 equivalents of 3-Amino-2,2-dimethyl-propan-1-ol (1.0 g, 10 mmol) in DMF in the presence of 2 equivalents of DIEA (1.7 ml, 10 mMol) is added a solution of sulfonylchloride (1b) (1.75 g, 5 mMol, 1 equivalent) in DMF. The reaction mixture is stirred for 12 h at room temperature. DCM is added and any excess of amine is extracted into 0.1N HCl solution. The organic phase is washed with brine and dried over MgSO$_4$. 4-Chloro-N-[5-(3-hydroxy-2,2-dimethyl-propylsulfamoyl)-thiophen-2-ylm-ethyl]-benzamide (compound of formula XII) is obtained after evaporation of the solvent. LC-MS analysis and NMR analysis showed that the compound was pure enough to carry on the next step.

Step 2—Alcohol Oxidation (Compound of Formula XIII)

Compound of formula XII (954 mg, 2.3 mmol, 1.0 eq.) obtained from step 1 was dissolved in 5 mL DMSO and Et$_3$N (3.0 eq.) was added to the mixture. Then, sulfur trioxide pyridine complex (3.0 eq.) dissolved in 10 mL of DMSO was further added to the reaction mixture which was stirred at room temperature for 2.5 h (until complete disappearance of the alcohol by TLC). HCl (1M) was added and the product was extracted with ethyl acetate. The organic phase was washed with HCl (1M) and then brine and dried with MgSO$_4$. The solvent was then evaporated. The aldehyde, 4-Chloro-N-[5-(2,2-dimethyl-3-oxo-propylsulfamoyl)-thiophen-2-ylm-ethyl]-benzamide (compound of formula XIII) was then purified by column chromatography using Ethylacetate/DCM(1/1).

Step 3—Reductive Amination (Compound of Formula I)

A solution of 4-Chloro-N-[5-(2,2-dimethyl-3-oxo-propyl-sulfamoyl)-thiophen-2-ylmethyl]-benzamide (formula XI) obtained from step 2 (0.41 g, 1 mMol, 1 eq.) and 3-((Trifluoromethyl)sulfonyl)-aniline (0.22 g, 1 mMol, 1 eq.) (formula XIV) in Tetrachloroethylen is heated at 110° C. in the presence of Molecular sieves 4 Å for 36 h. The reaction mixture is allowed to cool to room temperature and Sodiumcyanoborohydride (0.12 g, 2 mMol, 2 eq.) is added. The reaction is stirred for an additional 12 h at room temperature. The organic layer is washed with brine and dried over MgSO$_4$. The solvents are evaporated to dryness. The crude product is purified by preparative HPLC using an Acetonitrile/water gradient to yield to pure compound (16), 4-Chloro-N-{5-[2,2-dimethyl-3-(3-trifluoromethane-sulfonyl-phenylamino)-propylsulfamoyl]-thiophen-2-ylmethyl}-benzamide The following table provides HPLC data and mass spectroscopy data of the mentioned examples. [1],[2].

| Example | Name | HPLC[1] (Rt mn) | Mass[2] M + 1 | Mass[2] M - 1 |
|---|---|---|---|---|
| 16 | 4-Chloro-N-{5-[2,2-dimethyl-3-(3-trifluoromethanesulfonyl-phenylamino)-propylsulfamoyl]-thiophen-2-ylmethyl}-benzamide | 5.51 | 624 | 622 |

Example XVII

Preparation of a Pharmaceutical Formulation

The following formulation examples illustrate representative pharmaceutical compositions according to the present invention being not restricted thereto.

Formulation 1—Tablets

A sulfonamide compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active sulfonamide compound per tablet) in a tablet press.

Formulation 2—Capsules

A sulfonamide compound of formula I is admixed as a dry powder with a starch diluent in an approximate 1:1 weight ratio. The mixture is filled into 250 mg capsules (125 mg of active sulfonamide compound per capsule).

Formulation 3—Liquid

A sulfonamide compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A sulfonamide compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active sulfonamide compound) in a tablet press.

Formulation 5—Injection

A sulfonamide compound of formula I is dissolved in a buffered sterile saline injectable aqueous medium to a concentration of approximately 5 mg/mL.

Example XVIII

Biological Assays

Biological Results

The activities of the compounds according to formula I may be assessed using the following in vitro and in vivo biological assays.

JNK2 and -3 In Vitro Assays:

The phosphorylation of c-jun by JNK2 or JNK3 can be followed by monitoring the incorporation of $^{33}P$ into c-jun following the protocol below. The inhibitory activity of the compounds according to formula I, towards c-jun phosphorylation through JNK, is determined by calculating phosphorylation activity in the presence or absence of compounds according to formula I.

JNK3 and/or -2 assays are performed in 96 well MTT plates: incubation of 0.5 µg of recombinant, pre-activated GST-JNK3 or GST-JNK2 with 1 µg of recombinant, biotinylated GST-c-Jun and 2 µM $^{33}\gamma$-ATP (2 nCi/µl), in the presence or absence of compounds according to formula I and in a reaction volume of 50 µl containing 50 mM Tris-HCl, pH 8.0; 10 mM $MgCl_2$; 1 mM Dithiothreitol, and 100 µM $Na_3VO_4$. The incubation is performed for 120 min. at R.T and stopped upon addition of 200 µl of a solution containing 250 µg of Streptavidine-coated SPA beads (Amersham, Inc.)*, 5 mM EDTA, 0.1% Triton-X-100 and 50 µM ATP, in phosphate saline buffer. After incubation for 60 minutes at RT, beads are sedimented by centrifugation at 1500×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By replacing biotinylated GST-c Jun with biotinylated $GST\text{-}_1ATF_2$ or biotinylated myelin basic protein, this assay can be used to measure inhibition of preactivated p38 and ERK MAP Kinases, respectively.

The tested compounds according to formula I display an inhibition ($IC_{50}$) with regard to JNK3 of less than 10 µM, preferably less than 1 µM and more preferred less than 0.25 µM. For instance compounds (13) and (14) display an inhibition ($IC_{50}$) with regard to JNK3 of 188 nM and 184 nM respectively.

Il-2 Release Assay:

JNK pathway activation triggers the production of inflammatory cytokines such as IL-2. JNK can be activated by external stimuli such as PMA and Ionomycine and IL-2 production can be measured via an IL-2 ELISA test. Comparative measurements with and without the compounds of the invention according to the following protocol measure the ability of the compounds to prevent to stress-mediated IL-2 release.

Jurkat cells, a human T cell leukemia cell line (American Type Culture Collection # TIB 152) were cultured in RPMI 1640 medium (Gibco, BRL) supplemented with 10% of heat-activated fetal calf serum (TCS), Glutamine and Penstrep. The cell suspension in the medium is diluted to give $2.10^6$ cells/mL. The cells were plated ($2.10^5$ cells/well) on a 96-well plate containing different concentrations of a compound according to formula I (final concentration of compounds, 10, 3, 1, 0.3, 0.1 µM). This mixture is incubated 30 minutes at 37° C. in a humidified $CO_2$ atmosphere. Cells were then treated with 10 µl PMA (Phorbolmyristate-13 Acetate-12)+Ionomycine (0.1 µM and 1 µM final concentration) in all wells except negative control. In wells without compounds, 10 µl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

IL-2 ELISA Assay:

IL-2 release into the medium by (PMA+Iononomycin)-stimulated Jurkat cells, in presence or absence of test compounds may be assayed by ELISA. Following the procedure described below.

Monoclonal anti-human IL-2 antibody (MAB602) (capture), biotinylated anti-human IL-2 antibody (BAF202) (detection) and recombinant human IL-2 (202-IL-010) (standard) from From R&D Systems are used.

Plate Preparation

100 μl capture antibody diluted in PBS at 5 μg/ml (PBS—Tween 0.05%) are transferred into a 96 well ELISA plate and incubated overnight at room temperature. Each well is aspirated and washed 3 times with wash buffer (PBS—Tween 0.05%). After the last wash, the plate is damped.

Assay Procedure 1. 100 μl of sample or standard are added (2000, 1000, 500, 250, 125, 62.5, 31.25 pg/mL) and incubated 2 hours at room temperature.
2. 3-time-wash
3. 100 μl of biotinylated anti-human IL-2 at 12.5 ng/mL are added and incubated 2 hours at room temperature.
4. 3-time-wash
5. 100 μl streptavidin-HRP (Zymed #43-4323) at 1:10'000 are added and incubate 30 minutes at room temperature.
6. 3-time-wash
7. 100 μl substrate solution (citric acid/$Na_2HPO_4$ (1:1)+$H_2O_2$ 1:2000+OPD) are added and incubated 20-30 minutes at room temperature.
8. 50 μl of stop solution ($H_2SO_4$ 20%) are added to each well.
9. Optical density is measured using a microtiter plate reader set to 450 nm with correction at 570 nm.

C-Jun Reporter Assay

The phosphorylation of the transcriptional factor, c-jun, by JNK in the MAP kinase signal transduction pathway can be followed via a trans-reporting system such as the commercially available PathDetect® (33).

Inhibition of phosphorylation by compounds according to formula I can then be assessed.

A trans-reporting system allows one to follow, via Luciferase activity, the activation status of a fusion trans-activator protein. The trans-activator protein consists of the activation domain of the transcriptional factor of interest (c-jun) fused with a yeast transcriptional activator, GAL4 DNA binding domain (dbd). The GAL4 dbd has the advantage that no known mammalian transcriptional factors can bind to it and therefore the background noise of the assay is very low.

In the present case, Hela luciferase reporter-c-Jun (HLR-c-Jun) cell lines which constitutively express GAL4-cJun were used.

The MEKK-1 gene was inserted. MEKK-1 is a MAPKKK which triggers the activation of JNK. Expression of wild type MEKK-1 is sufficient for JNK activation (34).

Once, JNK is activated it can induce the phosphorylation of the c-jun domain of the fusion trans-activator protein (GAL4 dbd-cJun) which forms a dimer. The dimer is then is able to bind to a GAL4 upstream activating sequence (GAL4 UAS) of the reporter which activates Luciferase expression.

Luciferase expression is detected by luminescence using a simple assay such as Dual-Luciferase® Reporter Assay System (35) in which *Renilla* is used as a "control reporter".

Inhibition of JNK is observed as a decrease in Luciferase expression and detected by a decrease in luminescence.

Cell Culture

HLR-c-Jun cells are cultured in DMEM High Glc supplemented with 10% FCS (Sigma), 2 mM Glutamine (Gibco), P/S, Hygromycin b 100 μg/mL and G418 250 μg/mL.

Cell Culture Preparation

Cell Banks

The cells are stored frozen in cryotubes under liquid nitrogen, as 1.8 mL volumes of cell suspension in culture medium containing 10% dimethyl sulfoxide.

Cell Culture Thawing

When necessary, frozen vials of cells are thawed rapidly at 37° C. in a water bath by gently swirling up to semi-complete thawing. Then the cell suspension is added to 10 mL of culture medium and then centrifuged for 5 minutes at 1200 rpm. The supernatant is removed and the cell pellet reconstituted in the medium. The flasks are incubated at 37° C. in an atmosphere of 5% $CO_2$.

Cell Passage

The cells are serially sub-cultured (passaged) when 80% confluent monolayers have been obtained.

The medium of each flask is removed and the monolayer is washed with 10-15 mL of phosphate buffer solution (PBS).

Trypsin-EDTA solution is added to the cell monolayer, incubated at 37° C. and tapped gently at intervals to dislodge the cells. Complete detachment and disaggregation of the cell monolayer is confirmed by microscopy examination. The cells are then re-suspended in 10 mL of complete medium and centrifuged for 5 minutes at 1200 rpm. The supernatants are discarded, the cells are re-suspended in culture medium and diluted 1/5 in 175 $cm^2$ flasks.

Day 0 Morning

Prepare Cells for Transfections

The cells of near-confluent cultures are detached and dis-aggregated by treatment with trypsin as described above.

The cells are re-suspended in culture medium and counted.

The cell suspensions are diluted with medium to give about $3.5 \times 10^6$ cells/mL and 1 mL of cell suspension are put onto 2 10 cm culture dishes containing 9 mL of culture medium.

The plates are incubated at 37° C. in a humidified atmosphere of 5% $CO_2$ in air.

Day 0 Evening

Transfections

| Control: | 0.2 μg pTK Renilla, 5.8 μg pBluescript KS, 500 μl OPTIMEM (GIBCO), 18 μl Fugene 6. |
|---|---|
| Induced: | 0.1 μg pMEKK1, 0.2 μg pTK Renilla, 5.7 μg pBluescript KS, 500 μl OPTIMEM (GIBCO), 18 μl Fugene 6 30' RT. |

The transfection mixture is added to the plated cells. The plates are incubated over night at 37° C. in a humidified atmosphere of 5% $CO_2$ in air.

Day 1

A 96 wells plate (100l of culture medium per well) is prepared.

Negative control (vehicle): 2 μl of DMSO is added to the 100 μl (in triplicate).

2 μl of compound according to formula I stock dilutions (3, 1 and 0.1 mM in 100% DMSO) are added to the 100 μl (in triplicate).

The transfected cells are trypsinised and re-suspended in 12 mL of culture medium. 100 μl of the dilution are added to each of the 96 wells plate.

The plate is incubated over night at 37° C. in a humidified atmosphere of 5% $CO_2$ in air.

Day 2

Test procedure: Dual-Luciferase® Reporter Assay System (35).

The medium is removed from the plate and the cells are washed two times with 100 µl PBS. Lysis reagent is applied (Passive Lysis Buffer, PLB). Into each culture well 5 µl of 1×PLB are dispensed. The culture plates are placed on a rocking platform or orbital shaker with gentle rocking/shaking to ensure complete coverage of the cell monolayer with 1×PLB. The culture plates are rocked at room temperature for 15 minutes. 20 µl of the lysate are transferred into a white opaque 96 well plate. The luminometer reading is recorded.

~50 µl of Luciferase Assay Reagent II are injected and readings are recorded at 5 and 10 minutes.

50 µl of Stop & Glo® Reagent are injected and readings are recorded at 5 and 10 minutes.

The relative luminescence is then measured: RLU Luciferase/RLU *Renilla*.

LPS induced Endotoxin Shock in Mice

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ).

As LPS is known to stimulate the activation of various MAP kinase pathways, including JNK (36), the ability of JNK inhibitors can be tested after the JNK signaling pathway has been switched on by a LPS challenge.

The activity as JNK inhibitors of compounds of formula I may be assessed after a LPS challenge using the following protocol:

LPS (*S. abortus*-Galanos Lab.) is injected (200 µg/kg, i.v.) to Male C57BL/6 mice to induce endotoxin shock. Compounds according to formula I (0.1, 1, 10 mg/kg) or NaCl (200 uM) are injected intravenously (10 mL/kg) 15 min before the LPS challenge. Heparinized blood was obtained from the orbital sinus at different time points after the LPS challenge, and the blood was centrifuged at 9'000 rpm for 10 min at 4° C. to collect supernatant. Measurement of cytokines production such as TNFα and IFNγ by mouse is performed with an ELISA kit such as Duoset® DY410 for TNFα and DY 485 for IFNγ. Other ELISA assays such as described in (37) can be used.

Global Ischemia in Gerbils

The gerbil bilateral carotid occlusion is a well-described animal model of acute ischemic stroke and involves relatively easy surgical techniques.

The neuronal degeneration in the hippocampus develops over several days and is often referred as "delayed neuronal death". In addition, the neurodegeneration observed histologically is obvious and easily quantified (37). Furthermore, the histopathology seen in the gerbil is similar to that observed in the hippocampal CA1 region of the human brain following a cardiac arrest. Behavior observations, such as memory tests, could even be performed in the case of gerbils. This kind of tests for appreciation of the degree of recovery is not easily manageable in other models such as in rat whose learning abilities are much poorer (39).

The neuroprotective effect according to formula I to protect may be assessed using the gerbil global ischemia model and such a protocol:

—1—Method
 Surgery
  Anesthesia with isoflurane (0.5-4%).
  The common carotid arteries (left and right) are freed from tissue.
  Occlusion of the arteries using Bulldog microclamps during 5 min.
  Removal of clamps (reperfusion)
  Stabulation of the animals under heating lamp until awake.
  Stabulation of the animals in the animalry in individual cages.
 Sacrifice of the Animals
  7 days after ischemia (Decapitation or overdose of pentobarbital).
  Sampling of the brain.
 Histological parameters
  Freezing of the brain in isopentane (−20° C.)
  Slicing of the hippocampus using a cryo-microtome (20 µm).
  Staining with cresyl violet method
  Evaluation of the lesions (in CA1/CA2 subfields of the hippocampus) by a modified Gerhard & Boast score (40).

—2—Treatment
 Administration of the compound according to formula I or the vehicle: 15 min, 24 hours and 48 hours after reperfusion (5-10 min after the recovery of the anesthesia).
 Standard protocol
 50 animals: 5 groups of 8 (group A: control, groups B-D: test article at 3 doses and group E: reference compound (Orotic acid 3×300 mg/kg, ip).

REFERENCES

1. Davis, Roger J., Signal Transduction by the JNK Group of MAP Kinases. Cell, 2000, 103: 239-252.
2. Chen, Yi-Rong and Tan, Tse-Hua. The c-Jun N-terminal kinase pathway and apoptotic signaling. *International Journal of Oncology*, 2000, 16: 651-662
3. Ip, Y T. and Davis R J, Signal transduction by the c-Jun N-terminal kinase (JNK) from c-Jun N-terminal kinase (JNK) from inflammation to development *Curr Opin Cell Biol* 1998, 10:205-219.
4. Leppä, S, and Bohmann D., Diverse functions of JNK signalling and c-Jun in stress response and apoptosis, *Oncogene* 1999, 18(45):6158-6162.
5. Minden, A. and Karin M. Regulation and function if the JNK subgroup of MAP kinases. *Biochim Biophys Acta* 1997, 1333:F85-F104.
6. Whitmarsh, A. J., and Davis. R. J. Transcription factor AP-1: regulation by mitogen activated protein kinases signal transduction pathways. *J. Mol, Med.* 1996, 77, 2360-2371.
7. Gupta, S. et al., Selective interaction of JNK protein kinase isoforms with transcription factors. *The EMBO Journal*, 1996, 158(11): 2760-2770.
8. Derek D. et al., Absence of excitotoxicity-induced apoptosis in the hippocampus of mice lacking the Jnk3 gene. *Nature* 1997, 389:865-876.
9. Martin, Loel H. et al., Developmental expression in the mouse nervous system of the p49$^{3F12}$ SAP kinase. *Molecular Brain Research,* 1996, 35: 47-57.
10. Kumagae, Y. et al., Human c-Jun N-terminal kinase expression and activation in the nervous system, *Molecular Brain Research* 1999, 67: 10-17
11. Dumitru, Calin D. et al. TNF-alpha induction by LPS is regulated posttranscriptionally via a Tp12/ERK-dependent pathway. *Cell* 2000, 103: 1071-1083.
12. Han, Z. et al., C-Jun N-terminal kinase is required for metalloproteinase expression and joint destruction in inflammatory arthritis. *The Journal of Clinical Investigation* 2001, 108 (1):73-81.
13. Nishina, H., et al. Impaired CD28-mediated interleukin 2 production and proliferation in stress kinase SAPK/ERK1

14. Kempiak, Stephan J. et al. The Jun Kinase Cascade is responsible for activating the CD28 Response element of the IL-2 Promoter: proof of cross-talk with the IKB Kinase Cascade, *The Journal of Immunology*, 1999, 162: 3176-3187.
15. De la Monte, S. M. et al., Oxygen free radical injury is sufficient to cause some Alzheimer-type molecular abnormalities in human CNS neuronal cells. *J. Alzheimer's Dis.* 2000, 2(3-4): 261-281.
16. Zhu, X, Activation and redistribution of c-Jun N-terminal kinase/stress activated protein kinase in degenerating neurons in Alzheimer's disease. *Journal of Neurochemistry* 2001, 76: 435-441
17. Force, T. et al., Stress-Activated Protein Kinases in cardiovascular Disease. *Circulation Research*. 1996, 78:947-953.
18. Kim, S. et al., Angiotensin blockade inhibits activation of mitogen-activated Protein Kinases in Rat balloon-injured artery. *Circulation* 1998, 97:1731-1737.
19. Xu, Q. et al., Acute Hypertension Activates Mitogen-activated Protein Kinases in Arterial Wall. *The Journal of Clinical Investigation* 1996, 97 (2):508-514.
20. Bogoyevitch, M. A. et al., Stimulation of the stress-activated mitogen-activated protein kinase subfamilies in perfused heart. *Circulation Research.* 1996, 79:162-173.
21. Pombo, C M. et al., The stress-activated protein kinases are major c-Jun amino-terminal kinases activated by ischemia and reperfusion, *J. Biol. Chem.* 1994, 269 (42): 26546-26551.
22. Onishi, I. et al., Activation of c-Jun N-terminal kinase during ischemia and reperfusion in mouse liver, *FEBS Letters* 1997, 420: 201-204
23. Safirstein, R., Renal stress response and acute renal failure *Adv. Ren. Replace Ther.* 1997, 4 (2 Suppl 1): 38-42.
24. Butterfield, L. et al., C-Jun NH2-terminal kinase regulation of the apoptotic response of small cell lung cancer cells to ultraviolet. *The Journal of Biological Chemistry* 1997, 272 (15): 10110-10116.
25. Hu, M. et al., JNK1, JNK2 and JNK3 are p53 N-terminal serine 34 kinases, *Oncogene* 1997, 15: 2277-2287.
26. Xu, X et al., Constitutively activated JNK is associated with HTLV-1 mediated tumorigenesis, *Oncogene* 1996, 13: 135-142.
27. Chen Y R and Tan T H, The c-Jun N-terminal kinase pathway and apoptotic signaling, Int. J. Oncol 2000, 16(4): 651-62.
28. Harding, T. C. et al., Inhibition of JNK by overexpression of the JNK binding domain of JIP-1 prevents apoptosis in sympathetic neurons, *The Journal Of Biological Chemistry* 2001, 276(7):4531-4534.
29. Gennaro, A. R. et al., Remington's Pharmaceutical Sciences. 18th ed. Easton: The Mack Publishing Company, 1995.
30. Green T W and Wuts P G, 1999, 3$^{rd}$ Edition, Wiley Ed.
31. Scheibye et al., *Bull. Soc. Chim. Belg.* 1978, 87:229
32. Abdel-Magid A F et al., Reductive amination of aldehydes and ketones with sodium triacetoxyborohydride. Studies on direct and indirect reductive amination procedures, *Journal of Organic Chemistry* 1996, 61, 3849-62.
33. Xu, L. et al., Assess the in-vivo activation of signal transduction pathways with Pathdetect® reporting systems, *Strategies* 2001, 14 (1): 17-19.
34. Xu, S. et al., Cloning of rat MEK kinase 1 cDNA reveals an endogenous membrane-associated 195-kDa protein with a large regulatory domain, *Proc. Natl. Acad. Sci. USA* 1996, 93:5291-5295.
35. U.S. Pat. No. 5,744,320; Promega Corporation; Apr. 28, 1998
36. Guha, M. and Mackman, N., LPs induction of gene expression in human monocytes, *Cellular Signalling* 2001, 13: 85-94.
37. Fomsgaard, A. et al., Quantification and biological activities of native tumour necrosis factor from LPS-stimulated human monocytes, *APMIS* 1990, 98(6): 529-34.
38. Hunter J. L. et al., Animal models of acute ischaemic stroke: can they predict clinically successful neuroprotective drugs? *TIPS* 1995, 16:123-128.
39. Block, F., Global Ischemia And Behavioural Deficits, *Progress in Neurobiology* 1999, 58:279-295.
40. Gerhard S C and Boast C A, *Behavioral Neuroscience* 1988, 102: 301-303.

What is claimed is:

1. A sulfonamide according to formula I $$Ar^1-\underset{X}{\overset{\|}{C}}-\underset{R^1}{N}-(CH_2)_m-Ar^2-SO_2-\underset{R^2}{N}-[\underset{R^b}{\overset{R^a}{C}}]_n-[\underset{R^{b'}}{\overset{R^{a'}}{C}}]_p-N\diagdown\underset{R^4}{\overset{R^3}{}}$$

a geometrical isomer thereof, an optically active form thereof, an enantiomer thereof, a diastereomer thereof, a mixture thereof, or a salt thereof wherein:

$Ar^1$ is a substituted or unsubstituted aryl group;

X is O or S;

$Ar^2$ is a substituted or unsubstituted thienylene group;

$R^1$ and $R^2$ are independently selected from the group consisting of hydrogen and a $C_1$-$C_6$-alkyl group;

$R^a$, $R^{a'}$, $R^b$, $R^{b'}$ are independently selected from the group consisting of hydrogen and $C_1$-$C_6$-alkyl;

or $R^{a'}$ and $R^a$ or $R^{b'}$ together with the carbon atoms they are linked, form a substituted or unsubstituted 5-8-membered saturated, partially unsaturated or aromatic ring containing optionally one or more heteroatoms selected from O, N, S;

$R^3$ is selected from the group consisting of H, $C_1$-$C_{10}$-alkyl, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl $C_1$-$C_{10}$-alkyl;

or $R^3$ and $R^a$ or $R^{a'}$ form, together with the N atom linked to $R^3$, a 5-8-membered saturated ring, containing optionally at least one further heteroatom selected from O, N, S;

$R^4$ is selected from the group consisting of H and —C(H)$R^5R^6$;

$R^5$ and $R^6$ are independently selected from the group consisting of H, $C_1$-$C_{10}$-alkyl, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl $C_1$-$C_{10}$-alkyl;

m is an integer from 1 to 5;

n is an integer from 0 to 2; and p is an integer from 1 to 10;

wherein the compound according to formula I is selected from the group consisting of 4-Chloro-N-{5-[1-(4-trifluoromethyl-benzyl)-piperidin-3-ylsulfamoyl]-thiophen-2-ylmethyl}-benzamide;

4-Chloro-N-{5-[2,2-dimethyl-3-(4-trifluoromethyl-benzylamino)-propylsulfamoyl]-thiophen-2-ylmethyl}-benzamide;

4-Chloro-N-(5-{3-[methyl-(4-trifluoromethyl-benzyl)-amino]-propylsulfamoyl}-thiophen-2-ylmethyl)-benzamide;

4-Chloro-N-{5-[3-(hexyl-methyl-amino)-propylsulfa-moyl]-thiophen-2-ylmethyl}-benzamide;
4-Chloro-N-{5-[2-(4-trifluoromethyl-benzylamino)-cyclohexylsulfamoyl]-thiophen-2-ylmethyl}-benzamide;
4-Chloro-N-[5-(2 hexylamino-ethylsulfamoyl)-thiophen-2-ylmethyl]-benzamide;
4-Chloro-N-{5-[1-(4-trifluoromethyl-benzyl)-piperidin-4-ylsulfamoyl]-thiophen-2-ylmethyl}-benzamide;
4-Chloro-N-[5-(3-hexylamino-2,2-dimethyl-propylsulfamoyl]-thiophen-2-ylmethyl}-benzamide;
4-Chloro-N-{5-[3-(4-trifluoromethyl-benzylamino)-benzylsulfamoyl]-thiophen-2-ylmethyl}-benzamide;
4-Chloro-N-{5-[3-(4-trifluoromethyl-benzylamino)-propylsulfamoyl]thiophen-2-ylmethyl)benzamide;
4-Chloro-N (5-{[1-(4-trifluoromethyl-benzyl)-piperidin 3-ylmethyl]-sulfamoyl}-thiophen-2-ylmethyl)-benzamide;
4-Chloro-N (5-{methyl-[3-(4-trifluoromethyl-benzylamino)-propyl]-sulfamoyl}-thiophen-2-ylmethyl)-benzamide;
4-Chloro-N-{5-[(3-hexylamino-propyl)-methyl sulfamoyl]-thiophen-2-ylmethyl}-benzamide;
4-Chloro-N-(5-{[1-(4-trifluoromethyl-benzyl)-pyrrolidin-2-ylmethyl]-sulfamoyl}-thiophen-2-ylmethyl)-benzamide; and
4-Chloro-N-{5-[2,2-dimethyl-3-(3-trifluoromethanesulfonyl-phenylamino]-propylsulfamoyl]-thiophen-2-ylmethyl}-benzamide.

2. A medicament comprising the sulfonamide according to claim 1 and one or more pharmaceutically acceptable diluents or excipients.

3. A pharmaceutical composition comprising at least one sulfonamide according to claim 1 and one or more of a pharmaceutically acceptable carrier, diluent or excipient.

4. A process for the preparation of the sulfonamide according to claim 1 wherein $R^4$ is not H, comprising
reductively aminating a carbonyl group of formula VII with a compound of formula VI

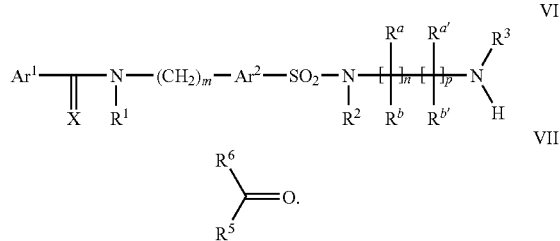

5. A process for the preparation of the sulfonamide, according to claim 1, wherein $R^4$ is H, comprising
deprotecting a compound of formula IV

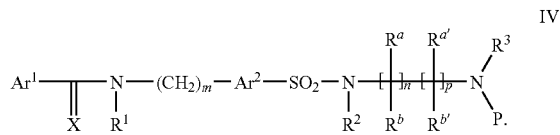

6. The process according to claim 4 wherein the compound of formula VI is obtained by deprotecting a compound of formula IV

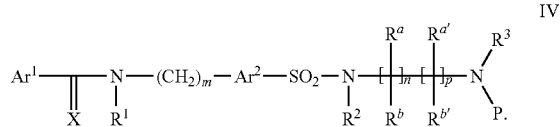

7. The process according to claim 5 wherein the compound of formula IV is obtained by reacting a compound of formula II with a compound of formula III

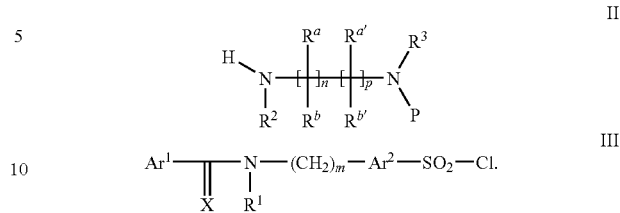

8. A process for the preparation of the sulfonamide according to claim 1, comprising
N-sulfonylating a compound of formula X with a sulfonylchloride of formula III

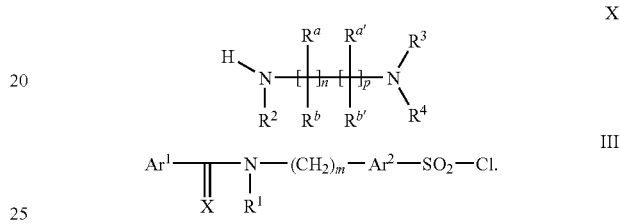

9. The process according to claim 8 wherein the compound of formula X is obtained by deprotecting a compound of formula IX

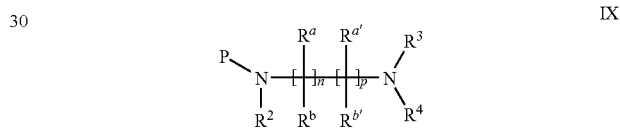

wherein P is a protecting group.

10. The process according to claim 9 wherein the compound of formula IX is obtained by reductively aminating a compound of formula VII with a compound of formula VIII

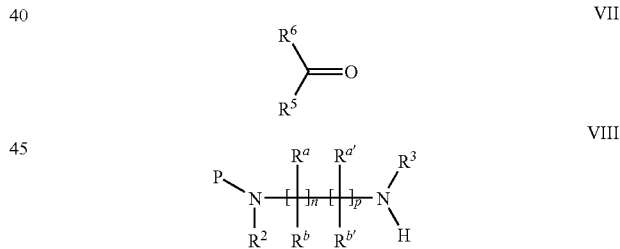

wherein P is a protecting group.

11. A process for the preparation of a compound of formula I, according to claim 1, comprising
reductively aminating a carbonyl group of formula XIII with an amine of formula XIV

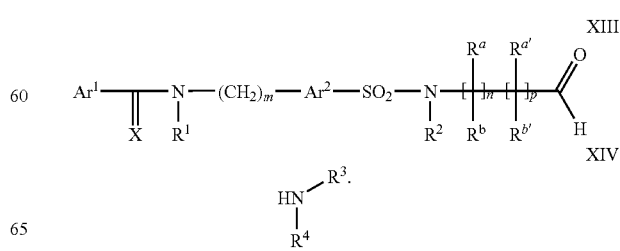

12. The process according to claim 11 wherein the compound of formula XIII is obtained by oxidizing a compound of formula XII
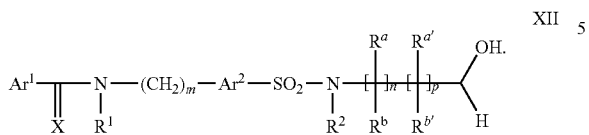
13. The process according to claim 12 wherein the compound of formula XII is obtained by sulfonylating a compound of formula XI
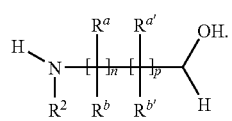
* * * * *

UNITED STATES PATENT AND TRADEMARK OFFICE
CERTIFICATE OF CORRECTION

PATENT NO. : 7,683,078 B2 Page 1 of 1
APPLICATION NO. : 10/484744
DATED : March 23, 2010
INVENTOR(S) : Rueckle et al.

It is certified that error appears in the above-identified patent and that said Letters Patent is hereby corrected as shown below:

On the title page, Item (86), the PCT information is incorrect. Item (86) should read:
--(86) PCT No.: PCT/EP02/07832

§ 371 (c)(1),
(2), (4) Date: Sep. 23, 2004--.

Signed and Sealed this

First Day of June, 2010

David J. Kappos
*Director of the United States Patent and Trademark Office*